United States Patent
Nimni et al.

(10) Patent No.: US 6,352,972 B1
(45) Date of Patent: *Mar. 5, 2002

(54) BONE MORPHOGENETIC PROTEINS AND THEIR USE IN BONE GROWTH

(76) Inventors: Marcel E. Nimni, 2800 Neilson Way, #908, Santa Monica, CA (US) 90405; Frederick L. Hall, 345 Pioneer Dr., Suite 1803, W. Glendale, CA (US) 91203; Lingtau Wu, 1114 Valencia Way, Arcadia, CA (US) 91006; Bo Han, 1351 Elm Ave., San Gabriel, CA (US) 91775; Edwin C. Shors, 2121 President St., Costa Mesa, CA (US) 92627

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,452

(22) Filed: Jun. 3, 1997

Related U.S. Application Data

(63) Continuation-in-part of application No. 08/470,837, filed on Jun. 6, 1995, now Pat. No. 5,800,811.

(51) Int. Cl.$^7$ .......................... A61K 38/18; C07K 14/51
(52) U.S. Cl. .......................... 514/12; 424/484; 424/426; 530/350
(58) Field of Search ................................ 424/419, 426, 424/484, 489, 192.1, 198.1; 514/12; 530/350

(56) References Cited

U.S. PATENT DOCUMENTS 5,270,181 A   12/1993   McCoy et al. ............. 435/69.7

FOREIGN PATENT DOCUMENTS

| EP | 0 433 225 A1 | * | 6/1991 |
| WO | WO 92/19746 | * | 11/1992 |
| WO | WO 96/39430 | | 12/1996 |

OTHER PUBLICATIONS

Ozkaynak et al. Osteogenic protein–2. A new member of the transforming growth factor–beta superfamily expressed early in embryogenesis. J Biol Chem, (Dec. 15, 1992) 267 (35)25220–7.*

Sampath et al. Recombinant human osteogenic protein–1 (hOP–1) induces new bone formation in vivo with a specific activity comparable with natural bovine osteogenic protein and stimulates osteoblast proliferation and differentiation in vitro. J. Biol. Ch Oct. 1992.*

Janknecht et al. Affinity purification of histidine–tagged proteins transiently produced in HeLa cells. Gene, Nov. 16, 1992) 121 (2) 321–4.*

Rudinger, J. "Characteristics of the amino acids as components of a peptide hormone sequence", in, Peptide Hormones, University Park Press, Jun. 1976.*

Alberts et al., Molecular Biology of the Cell, 1994, Garland Publishing, Inc., New York, NY, 1994.*

Bowie et al. Deciphering the message in protein sequences: tolerance to amino acid substitutions. Science, (Mar. 16, 1990) 247 (4948) 1306–10.*

Kingsley D M. The TGF–superfamily: new members, new receptors, and new genetic tests of function in different organisms. Genes and Development, (Jan. 1994) 8 (2) 133–46.*

Shah M; Foreman D M; Ferguson M W. Neutralization of TGF–1 and TGF–2 or exogenous addition of TGF–3 to cutaneous rat wounds reduces scarring. J. Cell Sci., (Mar. 1995) 108 (Pt 3) 985–1002.*

Reddi A. H. Role of morphogenetic proteins in skeletal tissue engineering and regeneration. Nat Biotechnol, (Mar. 1998) 16 (3) 247–52.*

Reddi A. H. Bone morphogenetic proteins: an unconventional approach to isolation of first mammalian morphogens. Cytokine Growth Factor Rev., (Mar. 1997) 8 (1) 11–20.*

Wang et al. Purification and characterization of other distinct bone–inducing factors. Proc Natl Acad Sci U S A, (Dec. 1988) 85 (24) 9484–8.*

Ngo et al., in The Protein Folding Problem and Tertiary Structure Prediction, Merz and Le Grand (Eds), Aug. 1994, Springer Verlag, pp. 433 and 492–495.*

Wozney et al. Growth factors influencing bone development. J Cell Sci Suppl 1990; 13:149–56.*

Sampath et al. Isolation of osteogenin, an extracellular matrix–associated, bone–inductive protein, by heparin affinity chromatography. Proc Natl Acad Sci U S A (Oct. 1987) 84(20):7109–13.*

Wozney J M. "Bone Morphogenetic Proteins and Their Gene Expression". Chapter 4, In, Cellular and Molecular Biology of bone, (M. Noda, ed.), pp. 131–167, Academic Press, San Diego, 1993.*

(List continued on next page.)

*Primary Examiner*—David S. Romeo
(74) *Attorney, Agent, or Firm*—Oppenheimer Wolff & Donnelly LLP

(57) ABSTRACT

A bone morphogenetic fusion protein and a method of preparation of the bone morphogenetic fusion protein. The bone morphogenetic fusion protein comprises a purification tag and a bone morphogenetic active fragment. A method of preparing bone morphogenetic fusion protein comprises purifying and renaturing bone morphogenetic protein to provide an active bone morphogenetic fusion protein preparation. Methods of use of the bone morphogenetic fusion protein are also provided.

2 Claims, 1 Drawing Sheet

OTHER PUBLICATIONS

QIAexpress® Detection and Assay Handbook. Second Edition. QIAGEN Inc., Valencia, CA, Apr. 1999, p. 10.*

A. H. Reddi and T. K. Sampath, Bone Morphogenetic Proteins Proteins Potential Role in Osteoporosis, Chapter 9, pp. 281–287 (1996).

A. H. Reddi, Clinical Orthopaedics and Related Research No. 313, pp. 115–119, Bone Morphogenetic Proteins, Bone Marrow Stromal Cells, and Mesenchymal Stem Cells. (Apr. 1995).

Wozney, John M. et al., "Novel Regulators of Bone Formation: Molecular Clones and Activities", *Science*, Dec. 16, 1988, vol. 242, pp. 1528–1534.

Sodek, Jaro et al., "Regulation of Osteopontin Expression in Osteoblasts", *Ann. N.Y. Acad. Sci.*, Apr. 21, 1995, vol. 760, pp. 223–241.

Copy of International Search Report for International Application No. PCT/US98/11189.

* cited by examiner

BONE MORPHOGENETIC PROTEINS AND THEIR USE IN BONE GROWTH

CROSS-REFERENCES

This application is a continuation-in-part application of application Ser. No. 08/470,837, filed Jun. 6, 1995, now U.S. Pat. No. 5,800,811.

BACKGROUND OF THE INVENTION

The Transforming Growth Factor beta (TGFβ) superfamily is a large group of cytokines that exert profound influences on the physiology of wound healing. Their mode of action in wound healing includes the modulation of stem cell populations, as well as their expression of specific genes that encode matrix proteins, cellular receptors, matrix proteinases and proteinase inhibitors. Numerous animal studies have demonstrated the efficacy of exogenous TGFβ in promoting wound healing, which lead to the first clinical applications in the repair of bone, surgical wound healing and in the treatment of diabetic ulcers and burns. Moreover, a single systemic dose of TGFβ$_1$, given prior to injury (surgery), has been demonstrated to enhance tissue repair and wound healing, suggesting that a single dose, administered systemically before surgery, may improve patient recovery rates.

Clinical studies using TGFβ$_1$ as a therapeutic agent have been hampered by its limited availability. TGFβ$_1$ is usually purified from either human platelets, bone or soft tissues such as placenta and kidney. It is estimated that approximately one ton of bone is required to purify enough TGFβ$_1$ for a single therapeutic treatment. Small amounts of TGFβ$_1$ have been isolated as a recombinant protein which was processed and secreted by transfected mammalian cells into conditioned growth medium. However, the small amounts of TGFβ obtained and the high cost of production do not make this a method of production commercially viable.

The potential utility of TGFβ$_1$ as a clinical agent to promote wound healing is complicated by TGFβ$_1$'s potent chemo-attractant and its macrophage and fibroblast activation properties. At elevated levels of TGFβ$_1$ such as occur in chronic fibrotic disorders, especially when local inflammation persists, macrophages and fibroblasts accumulate at the site of the disease. Elevated plasma levels of TGFβ$_1$ has been shown to correlate with a high incidence of hepatic fibrosis, and has also been associated with glomerulosclerosis and pulmonary fibrosis. Therefore, delivery to and activation of TGFβ$_1$ at the site of a wound is desirable for prolonged treatment with TGFβ$_1$.

Three distinct TGFβ polypeptides have been identified and are designated TGFβ$_1$, TGFβ$_2$ and TGFβ$_3$. The TGFβ proteins are expressed as precursor molecules of 380, 442 and 410 amino acids, respectively. These inactive latent TGFβ proteins are activated by proteinases such as plasmin, latent TGFβ$_1$ binding protein (LTBP) and thrombospondin. The mature form of the proteins are dimers of identical polypeptide chains of 112 amino acids in length. The amino acid sequence of the TGFβ$_1$, TGFβ$_2$ and TGFβ3 polypeptides shows 70 to 80% homology and the sequence conserved in the mature polypeptides includes 9 cysteine residues which determine the inter- and intra-polypeptide disulfide bridge formation in the mature proteins.

LTBP and a 60 kD TGFβ$_1$ binding protein appear to mediate the binding of TGFβ$_1$ to the extracellular matrix. The close association of TGFβ$_1$ with the extracellular matrix possibly maintains the elevated growth factor concentration within the local environment of the healing wound.

A subset of the TGFβ proteins are the bone morphogentic proteins (BMP). In postnatal life mammals continuously remodel their skeleton and retain the ability to initiate repair in response to injury and trauma. The cellular and molecular basis for this bone morphogenesis and repair has been attributed to the BMP's and their responding inducible osteogenic precursor cells. Bone marrow has cells with osteogenic potential and consists of determined osteogenic precursor cells that are committed to osteogenesis. Determined osteogenic precursor cells can differentiate into bone without an exogenous signal. Inducible osteogenic precursor cells requires a molecular signal for initiating the differentiation program. BMP's effects include: chemotaxis of monocytes and mesenchymal cells, mitosis of mesenchymal progenitor cells; initiation of differentiation; inhibition of proliferation of differentiated cells; promotion of osteoblast phenotype; maintenance of bone; and cartilage phenotype and binding to extracellular matrix.

The BMP's include at least 9 different proteins, named: BMP-2 (also known as BMP-2A); BMP-3 (also known as osteogenin); BMP-4 (also known as BMP-2B); BMP-5; BMP-6; osteogenic protein-1 (OP-1, also known as BMP-7); osteogenic protein-2 (OP-2, also known as BMP-8); BMP-3b and GDF-10 (also known as BMP-10). There are several subgroups among the BMP's as follows: BMP-2 and 4; BMP-5 to 8; and BMP-3 and GDF-10 share physical properties. All BMP's are expressed as a protein of about 300 to about 400 amino acid residues. The proteins are subsequently processed to a mature region having between about 100 to about 200 amino acids at a consensus sequence of Arg-X-X-Arg SEQ ID NO: 49.

The use of TGFβ or BMP-based medical therapies require the availability of large quantities of pharmaceutical grade TGFβ and BMP that is free of transmittable hazards omnipresent in products extracted from animal, in particular human, sources. Therefore, it is desirable to develop a means for preparing large quantities of the mature TGFβ and BMP. It is also desirable that the protein(s) is (are) made from a source which eliminates the possibility of hazardous material contaminating the final product. It is also desirable that the protein is engineered to target specific sites where wound healing is desired.

SUMMARY OF THE INVENTION

The present invention is directed at a bone morphogenetic fusion protein, a method of preparation of the bone morphogenetic fusion protein and methods of using the bone morphogenetic fusion protein.

The bone morphogenetic fusion protein comprises a purification tag and a bone morphogenetic active fragment.

The method of preparation bone morphogenetic fusion protein comprises purifying and renaturing bone morphogenetic protein to provide an active bone morphogenetic fusion protein preparation.

Methods of use of the bone morphogenetic fusion protein include methods to promote bone growth at the site of a fracture and as a replacement for bone in performing bone grafts.

BRIEF DESCRIPTION OF THE DRAWINGS

Features, aspects and advantages of the invention will be more fully understood when considered with respect to the following detailed description, appended claims and accompanying drawing where:

DETAILED DESCRIPTION

Figure 1:
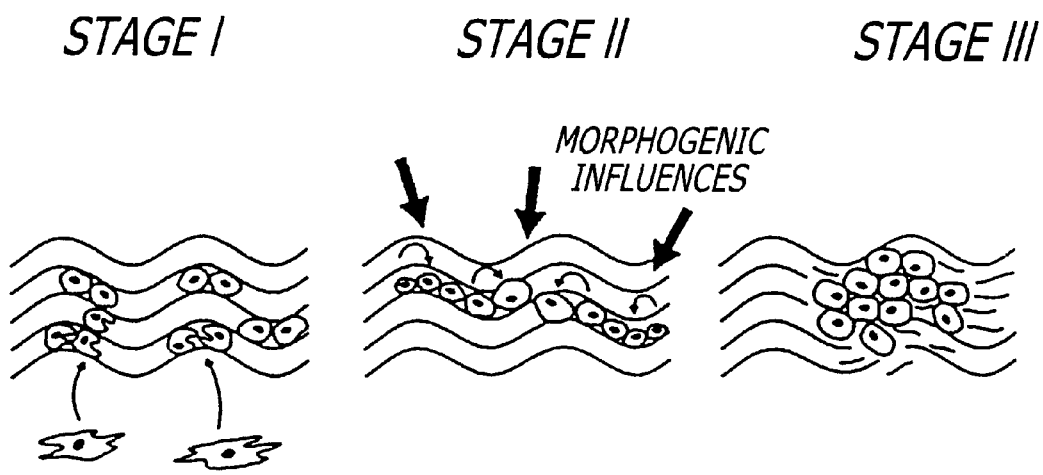
FIG. 1 is a diagrammatic representation of the stages of wound healing observed with TGFβ treated collagen matrices.

This invention is directed at genetically engineering TGFβ and/or BMP (TGFβ/BMP) fusion proteins, their expression in *E. coil* and their purification and renaturation of active TGFβ/BMP. As used herein TGFβ, TGFβ$_1$, TGFβ$_2$, TGFβ$_3$, BMP-2, BMP-3, BMP-4, BMP-5, BMP-6, BMP-7, BMP-8, BMP-10 and BMP-3b means the active portion of TGFβ, TGFβ$_1$, TGFβ2, TGFβ$_3$, BMP-2, BMP-3, BMP-4, BMP-5, BMP-6, BMP-7, BMP-8, BMP-10 and BMP-3b, respectively, present in the mature form of the naturally occurring proteins or other such proteins which exhibit similar biological activity. Also, as used herein, transforming growth factor-β fusion protein or BMP fusion protein means the active portion of TGFβ, TGFβ$_1$, TGFβ$_2$, TGFβ$_3$, BMP-2, BMP-3, BMP-4, BMP-5, BMP-6, BMP-7, BMP-8, BMP-10 and BMP-3b produced in accordance with this invention and may include other regions such as purification tags, as described below. Transforming growth factor-β and BMP fusion protein is also intended to mean the active portion of TGFβ, TGFβ$_1$, TGFβ2, TGFβ$_3$, BMP-2, BMP-3, BMP-4, BMP-5, BMP-6, BMP-7, BMP-8, BMP-10 and BMP-3b which has been cleaved from other domains such as purification tags. The ability to express and renature the active fragment of TGFβ or BMP in the absence of the pro-region, in accordance with the present invention, into a biologically active dimer is a surprising result. Other workers in the field have concluded that their experiments demonstrate that the pro-region of TGFβ or BMP is essential for the folding and assembly of TGFβ or BMP dimers. Therefore, in view of the teaching in this field, expression of the active portion of TGFβ or BMP, in the absence of the pro-region, would not be expected to result in a biologically active dimer.

The present invention is also directed at the use of these proteins in the treatment of wound healing and bone growth.

In accordance with this invention a prokaryotic expression vector is engineered to produce a fusion proteins which comprise a cDNA sequence encoding the active fragment of human TGFβ$_1$, TGFβ$_2$, TGFβ$_3$, BMP-2, BMP-3, BMP-4, BMP-5, BMP-6, BMP-7, BMP-8, BMP-10 or BMP-3b by methods well known to those skilled in the art. Additionally, the fusion proteins may comprise a purification tag, proteinase-sensitive linker sites and binding domain such that the protein sequence may contain all or some of the following elements:

purification tag:proteinase site:ECM/bone binding site: proteinase site:TGFβ/BMP Amino acid sequences suitable for use as the elements above are in the sequence listing and are summarized as follows:

Purification tag: SEQ ID NOs: 22, 24, 26 and 28;
Proteinase site: SEQ ID NOs: 1 to 11, 13 and 15;
ECM binding site: SEQ ID NOs: 16, 18 and 20; and
TGFβ or BMP: 30, 32, 34 and 36.

While these sequence are provided, one skilled in the art will be aware of other sequences which perform the equivalent function as the sequences listed above which could be substituted for the sequences in the sequence listing.

The inclusion of a purification tag facilitates purification of the fusion protein. A first proteinase site is included to permit cleavage and release of the purification tag after purification of the fusion protein, if desired.

The binding site facilitates delivery of the fusion protein to the desired site of action. The binding site is, therefore, chosen to direct the TGFβ/BMP to the site to be healed or where bone growth is required. Delivery of the TGFβ/BMP to the site to be treated reduces the amount of TGFβ/BMP required to be administered to be effective and reduces the concentration of circulating TGFβ/BMP which may result in undesirable side effects. Additionally, the binding of the TGFβ/BMP to the desired target site prevents or inhibits diffusion of the TGFβ/BMP from the target site thus increasing the dose of the TGFβ/BMP at the target site.

In some circumstances it is also desirable to included a second proteinase binding site, which may be the same as or different from the first proteinase site. Where the second proteinase site is different from the first proteinase site, the second proteinase site allows the TGFβ/BMP to be released from the binding site once it has reached its site of action. Proteolysis occurs as a result of the action of endogenous proteinases released at the site of the injury. Since the release of the proteinases is over a period of time, as the healing process proceeds, the TGFβ/BMP is also released slowly, over a period of time. Therefore, a second proteinase site is used where such "time release" is desirable. In applications where release of the TGFβ/BMP is undesirable, the second proteinase site is omitted.

In one embodiment of the present invention binding domains are used which are selective for either collagen, fibronectin or cell surface.

In one embodiment of the present invention the sequence selective for collagen was modified (collagen$^m$), from the naturally occurring sequence of:

Trp-Arg-Glu-Pro-Ser-Phe-Cys-Ala-Leu (SEQ ID NO: 50) to:

Trp-Arg-Glu-Pro-Ser-Phe-Met-Ala-Leu (SEQ ID NO: 51)

to ensure that the Cys would not interfere with the refolding/renaturation of the TGFβ.

In the case of BMP, binding sites present in bone are used. In this case it may be desirable to use the purification tag (His)$_6$ as the binding domain since (His)$_6$ bind to the hydroxyapatites of bone. Those skilled in the art will be aware of other suitable binding domains which could be substituted of the (His)$_6$ binding domain which would result in binding of the fusion protein to bone.

Illustrative combinations of fusions proteins suitable for use in the present invention are summarized in Table I. The list in Table I is intended to illustrate some of the types of fusion proteins which are intended by the present invention and are not intended to limit the scope of the invention. Those skilled in the art will be aware that practice of the present invention could include other elements such as: other purification tags, such as epitope tags and specific binding proteins, enzymes, ribonuclease S (SEQ ID NO: 24), glutathione S-transferase (SEQ ID NO: 26) and hemagglutinin (SEQ ID NO: 28); other proteinase sites, such as thrombin cleavage site (SEQ ID NO: 14 and 15), factor Xa cleavage site (SEQ ID NO: 12 and 13), plasmin cleavage site (SEQ ID NO: 1), chymotrypsin cleavage site (SEQ ID NO: 2 and 3), elastase cleavage site (SEQ ID NO: 4 and 5), trypsin cleavage site (SEQ ID NO: 6 and 7), pepsin cleavage site (SEQ ID NO: 8 and 9), thermolysin cleavage site (SEQ ID NO: 11), other binding sequences such as cell surface and tissue specific antigens, extracellular matrix binding site (SEQ ID NO: 16), fibronectin (SEQ ID NO: 18), collagen (SEQ ID NO: 20) and other TGFβ's fragments, such as TGFβ$_2$ (SEQ ID NO: 32), TGFβ$_3$ (SEQ ID NO: 34), BMP fragments such as the fragment from EMP-3 (SEQ ID NO: 36), fragments could be substituted for TGFβ$_1$. One skilled in the art will also be aware that modifications of the sequences of these elements could also be used which would not change the functional properties for which they are used. Those skilled in the art will also realize that "linkers" could be added between the elements, to facilitate cloning and manipulation of the resultant clones without changing the functional properties of the resultant fusion proteins.

TABLE I

| Tag | proteinase site | Binding domain | proteinase site | TGFβ | SEQ ID NO. |
|---|---|---|---|---|---|
| (His)$_6$ | none | none | none | TGFβ$_1$ | 22:30 |
| (His)$_6$ | thrombin | none | none | TGFβ$_1$ | 22:15:30 |
| (His)$_6$ | thrombin | collagen$^m$ | none | TGFβ$_1$ | 22:15:20:30 |
| (His)$_6$ | thrombin | collagen$^m$ | thrombin | TGFβ$_1$ | 22:15:20:15:30 |
| (His)$_6$ | thrombin | collagen$^m$ | factor Xa | TGFβ$_1$ | 22:15:20:13:30 |
| (His)$_6$ | factor Xa | none | none | TGFβ$_1$ | 22:13:30 |
| (His)$_6$ | factor Xa | collagen$^m$ | none | TGFβ$_1$ | 22:13:20:30 |
| (His)$_6$ | factor Xa | collagen$^m$ | factor Xa | TGFβ$_1$ | 22:13:20:13:30 |
| (His)$_6$ | factor Xa | collagen$^m$ | thrombin | TGFβ$_1$ | 22:13:20:15:30 |
| (His)$_6$ | thrombin | fibronectin | none | TGFβ$_1$ | 22:15:18:30 |
| (His)$_6$ | thrombin | fibronectin | thrombin | TGFβ$_1$ | 22:15:18:15:30 |
| (His)$_6$ | thrombin | fibronectin | factor Xa | TGFβ$_1$ | 22:15:18:13:30 |
| (His)$_6$ | factor Xa | fibronectin | none | TGFβ$_1$ | 22:13:18:30 |
| (His)$_6$ | factor Xa | fibronectin | factor Xa | TGFβ$_1$ | 22:13:18:13:30 |
| (His)$_6$ | factor Xa | fibronectin | thrombin | TGFβ$_1$ | 22:13:18:15:30 |

In the practice of the present invention, fusion protein expression vectors are expressed in *E. coli* or other suitable hosts and are isolated and purified. The proteins of the present invention expressed in bacteria accumulate in inclusion bodies in a precipitated form. In such cases it is desirable to solubilize the protein in a denaturing, or other suitable buffer for further purification. Such denaturing buffers include a denaturing agent such as 8 M urea and may also include reducing agents such as dithiothreitol (DTT) or β-mercaptoethanol.

In one embodiment of the present invention the purification of the fusion proteins uses a purification tag comprising polyhistidine expressed as an N-terminal portion of the fusion protein. When the purification tag comprises polyhistidine, a metal chelate binding medium such as nickel chelate medium is used as the purification medium. In other embodiments of the present invention the purification tag comprises epitopes, schistosoma japonicum glutathione S transferase (GST), ribonuclease S or Hemagglutinin, and the binding medium comprises PBS with an eluting agent such as low pH and peptides or glutathione. Other purification tags, their associated binding media and suitable conditions for binding and eluting the proteins from the media are summarized in Table II.

TABLE II

| Tag | Binding Medium | Binding Buffer | Elution Buffer |
|---|---|---|---|
| (His)$_6$ | metal chelate | denaturing buffer, pH 6.5 | denaturing buffer, pH 4.0 |
| Ribonuclease S | S-protein agarose | PBS | PBS + low pH or peptides |
| GST | affinity medium | PBS | PBS + low pH or glutathione |
| Hemagglutinin A | Immuno-affinity | PBS | PBS + low pH or peptides |

Proteins are isolated from host cells transformed with TGFβ fusion protein expression vector and proteins are solubilized in a denaturation buffer adjusted to a pH of about pH 8.0. Suitable denaturation buffers are comprise a high concentration of a denaturant such as 8 M urea. Such buffers may also comprise a reducing agent such as β-mercaptoethanol. Any particulate material in the solubilized protein sample is removed by centrifugation at about 20,000×g for about 20 minutes.

The supernatant, which includes TGFβ/BMP fusion protein, is collected and mixed with a metal chelate medium such as Ni-NTA resin and gently agitated for about 1 hour. The TGFβ/BMP fusion protein/resin mixture is then loaded onto a column, the resin is allowed to settle and the liquid is drained off. The protein/resin mixture is washed with denaturation buffer adjusted to a pH of about 8.0 to remove non-specifically bound proteins. Additional non-specifically bound proteins are eluted by washing the protein/resin mixture with denaturation buffer, adjusted to pH of about 6.5. The TGFβ/BMP fusion protein is then eluted from the metal chelate medium by washing with denaturation buffer adjusted to a pH of about 4.0 and the eluted proteins, which include TGFβ/BMP, are collected.

The eluate is diluted to a protein concentration of about 0.05 to about 0.5 mg/ml with denaturation buffer and adjusted to a pH of about 8.0. The diluted protein sample is then further diluted with about 4 volumes of freshly made buffer such as about 20 mM Tris-HCl, pH 8.0, about 250 mM NaCl, about 0.05% (v/v) NP-40, about 2 mM reduced glutathione and about 0.2 mM oxidized glutathione.

The diluted protein is sealed in a container and stored overnight at about 4° C. The diluted protein is then dialyzed against an equal volume of a dialysis buffer such as about 20 mM Tris, pH 8.0, about 250 mM NaCl and about 20% (v/v) glycerol for about 20 minutes. After about 20 minutes, and then about every 20 minutes thereafter, the dialysis buffer is replaced with twice the volume of dialysis buffer previously used, until the final volume is about 10 times the volume of the dialysate. The dialysis is then stored overnight at about 4° C. without stirring. The next morning the dialysis is stirred for about 30 minutes. The dialysis buffer is then replaced and the dialysis is stirred for about 2 hours. The contents of the dialysis bag is then collected and any particulate matter is removed by centrifugation at about 5,000 rpm for about 20 minutes at 4° C.

The TGFβ fusion protein isolated, purified and renatured as described above, exhibits an antiproliferative activity comparable to TGFβ$_1$ controls (naturally occurring TGFβ$_1$).

The present invention is also directed at the use of TGFβ fusion proteins in wound healing.

It is desirable to administer the TGFβ of the present invention as a preventative measure prior to surgery. In such cases, TGFβ prepared in accordance with the process of the present invention, is administered as a single dose of 100 to 500 μg/ml/kg body weight, intravenously, about 24 hours prior to surgery.

The present invention is also directed at a mesenchymal stem cell trap. FIG. 1 is a diagram of wound healing stages observed within TGFβ treated collagen matrices. Depicted are three major features: (I) recruitment and expansion of a mesenchymal stem cell (MSC) population, (II) elaboration (of factors) and differentiation of cellular phenotype and (III) resolution and remodeling of the extracellular matrix. TGFβ impregnated collagen matrices are utilized to selectively reinforce the proliferation of mesenchymal stem cells that are present in low abundance within human bone marrow aspirates under conditions where the remainder of the cellular components of the marrow do not survive. Rescue and selection of TGFβ responsive stem cells from human bone marrow aspirates is performed after about 15 days of serum deprivation. Serum deprivation results in the death of unwanted cells.

The present invention is also directed at the use of genetically engineered TGFβ fusion proteins, produced in prokaryotes, for therapeutic advantage in the clinical management of ex vivo histogenesis, the preparation of "Artificial Skin" and surgical wound healing. Collagen matrices and sheets which are currently used as a "skin or tissue replacement", though optimal in terms of structural integrity and biodegradability, are highly antigenic in wound healing applications, resulting in inflammatory responses (rejection) and fibrosis (scarring). In contrast, TGFβ impregnated collagen matrices inhibit inflammatory processes while promoting angiogenesis and histogenesis. TGFβ is a natural and critical component regulating epithelial-mesenchymal interactions in the developmental morphogenesis of skin appendages. Collagen bound TGFβ fusion proteins function effectively to select and expand (capture) a population of mesenchymal stem cells in vitro.

An autologous "artificial" skin is prepared by selecting and expanding a population of explanted human fibroblasts, along with other resident mesenchymal precursors, within TGFβ impregnated collagen sheets. This procedure is continued in vitro up to an optimized point whereby the collagen sheet is effectively cellularized yet not degraded. At or just prior to this point, the collagen/connective tissue sheet is epithelialized by the application of an explanted plug of keratinocytes.

The human artificial skin comprised of TGFβ impregnated matrix such as collagen sheets is cellularized and epithelialized in a 2-stage process:

1. Enrichment (recruitment and expansion) of pluripotent stem cells facilitate normal histogenesis and wound healing. Recombinant TGFβ fusion proteins are applied to the cellularized "skin" (i.e., cellularized/epithelialized collagen sheets) and/or the wound surface.

2. Secondary application of TGFβ fusion proteins inhibits rejection and promotes fusion of cultured tissues The timing of each stage of the ex vivo tissue culture, as well as the thickness and physiochemistry of the collagen sheets, are determined by visual observation. The TGFβ fusion proteins play a pivotal role in promoting normal skin healing while suppressing the inflammatory responses and granulation tissue associated with chronic wounds.

Frequently, the fusions of long bones after a fracture are unsuccessful and cartilage, rather than bone, is formed at the fracture resulting in a "non-union." The presence of cartilage in such fracture unions results in movement and the requirement for surgical intervention to repair the fracture. In other cases, such as in the case of spinal fusions, bone is removed from one part of the body, usually the hip, for placement at the site of the fusion. These procedures subject the patient to extended surgical procedures resulting from the need to remove bone from the hip and to extended recovery, not only from the target surgery but also at the "donor" surgical site.

BMP of the present invention promotes the calcification at a desired site. For use, a matrix such as ceramic pads (made from hydroxyapatite) or other suitable matrices are impregnated with a "site" for recognition and binding of the BMP of the present invention. Suitable sites for use in the present invention are those such as collagen, hydroxyapatite or other sites for which a DNA sequence encoding a suitable binding domain can be incorporated into a construct with a DNA sequence encoding a mature BMP protein. Such sites and binding domains which recognize the sites are well known to those skilled in the art. A DNA sequence encoding the mature region of a BMP is constructed with a DNA sequence encoding a purification code and a binding domain. The binding domain and the purification tag may be the same domain. Poly histidine is preferred as the purification tag and also as the binding domain, since poly histidine will bind to hydroxyapatite when it is use as the site in the matrix. BMP, with the binding domain is impregnated into the matrix where it binds to the sites present in the matrix. The BMP impregnated matrix is then implanted at the desired site of bone growth. For example, when poly histidine is used as the binding domain and hydroxyapatite is use as the site within the matrix the poly histidine tag binds to the hydroxyapatite and thus also binds the BMP mature region. Binding of the BMP to the hydroxyapatite localizes the BMP to the desired site to activate ostiogenesis. Also, the BMP is released from the hydroxyoatite at a very slow rate so that over time BMP is slowly released into the surrounding tissue to further stimulate ostiogenesis.

EXAMPLE 1

Recombinant Constructs and Protein Expression

Cytoplasmic RNAs isolated from EW-1 Ewing's sarcoma cells and human MG-63 osteosarcoma cells were reverse transcribed into first-strand cDNA using an antisense oligonucleotide primer by methods well know to those skilled in the art. PCR amplification was performed on the first strand cDNA and the resulting PCR products were separated electrophoretically, by methods well know to those skilled in the art. Visualized bands were purified from agarose gel by Geneclean (Bio 101) and ligated to a TA vector (Invitrogen) Color-selected clones were isolated and analyzed by restriction mapping, followed by nucleotide sequence determination.

To construct a tripartite fusion protein the cDNA sequence encoding the C-terminal 112 amino acids of human $TGF\beta_1$, obtained by RT-PCR, was ligated in frame to pET28 vector (Novagen), and maintained in the XL Blue strain of E. coli BL21 (DE3). The orientation and reading frame of the insert was confirmed by DNA sequence analysis.

Each of the $pET-TGF\beta_1$ constructs were transformed into E. coli BL21(DE3), and high level expression of recombinant proteins was induced in the presence of 0.4 mM isopropyl thiogalactopyranoside (IPTG) for 5 hours at 37° C. with shaking at 300 rpm. The first construct, $pET-TGF\beta_1$-Thrombin, contained a $(His)_6$ leader sequence at the N-terminus of the fusion protein, a thrombin cleavage site in the first proteinase site, followed by a truncated active $TGF\beta_1$ fragment (i.e. the plasmid encoded SEQ ID NOs. 22:15:30). Two additional constructs, $pET-TGF\beta_1$-Thrombin-Collagen and $pET-TGF\beta_1$-Thrombin-Fibronectin, which incorporated, in addition to the thrombin proteinase site collagen-binding and fibronectin-binding sites, respectively (i.e. the plasmids encoded SEQ ID NOs. 22:15:20:30 and SEQ ID NOs. 22:15:18:30, respectively), were designed for extracellular matrix targeting of these fusion proteins.

EXAMPLE 2

Small Scale Induction of Recombinant TGFβ Fusion Proteins in E. coli

E. coli, BL21(DE3), transformed with $pET-TGF\beta_1$-Thrombin, prepared as described above, with a protein tag of 6 Histidine residues at the N-terminal of the fusion protein was inoculated into 5 ml of 2×YT medium in the presence of kanamycin (50 μg/ml kanamycin sulfate, supplied by GIBCO-BRL). The cultures were incubated at 37° C. with shaking (225 rpm; Lab-Line orbital shaker) until visible bacterial growth was observed, about 2 to 3 hours.

Three ml of cell suspension was transferred to 12 ml of YT medium which included 50 μg/ml kanamycin sulfate. The cultures were incubated at 37° C. with shaking (225 rpm) until visible bacterial growth was observed, about 2 to 3 hours. The cultures were then monitored at $A_{600}$. When the cultures reached $A_{600}$ of 0.6 to 0.8 the expression of the fusion protein was induced by the addition of IPTG (Sigma I-6758) to a final concentration of 0.4 mM. The cultures were incubated at 37° C. with shaking at 300 rpm.

The remaining 2 ml of the original culture, the pre-induction samples, were centrifuged in a microfuge (Eppendorf 5415C) at 10,000 rpm for 2 minute and the supernatant aspirated. Two hundred μl of SDS sample buffer (reducing) was added to the cell pellet and the sample was mixed and heated at 95° C. to 98° C. for 7 minutes. The pre-induced samples were stored at −20° C. until needed.

After 3.5 to 4 hours of incubation in the presence of IPTG, 1 ml aliquots of the cultures were removed and centrifuged as described above for the uninduced samples. The cell pellet was dissolved in 300 μl SDS sample buffer (reducing) and heat at 95° C. to 98° C. for 7 minute. The induced samples were stored at −20° C. until needed.

The remainder of the cells were collected by centrifugation at 2,000 to 3,000 rpm for 10 minute. The cell pellets were frozen at −20° C. until needed.

EXAMPLE 3

Gel Electrophoresis and Protein Staining

Ten μl of each of the pre-induction and induced samples prepared as described in Example 2, were loaded, per lane, on a 8 to 16% gradient gel (1.5 mm thick). Five to 10 μl of protein standard (e.g., Novex) were included on the gel in separate lanes. The gels were run in standard SDS gel electrophoresis buffer at 100 to 125 volts for 2 to 2.5 hours until the dye front reached the bottom of the gel. The gel was fixed in 40% (v/v) methanol, 10% (v/v) acetic acid for 20 minutes with gentle shaking. The gel was then stained with 0.25% (w/v) Coomassie blue stain (in 50% (v/v) methanol, 10% (v/v) acetic acid) for 20 minutes. The gel was then destain twice (1 to 2 hours each time) in 40% (v/v) methanol, 10% (v/v) acetic acid. The gels were then viewed over a light box to determine, qualitatively, the level of induction.

Finally, the gel was destained overnight in 10% (v/v) methanol, 10% (v/v) acetic acid, dried and stored.

EXAMPLE 4

Small Scale Induction of Recombinant TGFβ Fusion Proteins in *E. coli*

A clone with a high induction response determined by the process of Examples 1 to 3 was selected and 200 μl of a 3 to 4 hour culture was added to 20 ml of medium supplemented with 50 μg/ml kanamycin. The culture was incubated at 37° C. with shaking at 225 rpm overnight. Ten ml of the overnight culture was inoculated into 500 ml medium supplemented with 50 μg/ml kanamycin. The $A_{600}$ of the cells was monitored. When the $A_{600}$ reached 0.7 to 0.8, 1 ml aliquots were collected, centrifuged and the cell pellet denatured as described in Example 2. This sample represented the pre-induction sample.

Five hundred μl IPTG was added to the culture and the culture was incubated with shaking at 275 rpm for 4 to 5 hours. A 1 ml aliquot was collected for the induced sample.

Cells in the remaining culture were collected by centrifugation at 4° C. at 8,000 rpm (7,500×g) for 15 minute. The supernatant was decanted and the cell pellets were stored at −20° C.

Induction of the pET-TGFβ$_1$-Thrombin fusion protein in the BL21(DE3) strain of *E. coli* in the presence of IPTG resulted in high yield expression of the 12.5 kD His-tagged C-terminal active fragment of TGFβ$_1$. The vast majority of the expressed protein was found sequestered in insoluble inclusion bodies in the *E. coli*. The expressed protein was recovered by solubilization in 8 M urea followed by Ni-NTA chelate chromatography.

EXAMPLE 5

Renaturation of Recombinant TGFβ$_1$-Thrombin

Solubilization and refolding of recombinant TGFβ$_1$-Thrombin fusion protein was performed under a variety of experimental conditions.

Method I: A single step method used low concentrations of urea and DTT.

Method II: A redox system used DTT in conjunction with glutathione.

Method III: A modification of the glutathione redox system involved a slow dilution of the urea-solubilized material (solubilized in 10 mM Tris base, 100 mM Na$_2$HPO$_4$, and 8 M urea, pH 8.0) with a balanced redox buffer (2 mM reduced glutathione, 0.2 mM oxidized glutathione, 20 mM Tris-HCl, pH 8, 250 mM NaCl, 0.05% NP-40; NP-40 supplied by Sigma N0896 for 48 hours prior to dialysis).

In each case, the renatured preparation was dialyzed in protracted steps against Tris buffer (20 mM Tris-HCl, pH 8.0, 500 mM NaCl, 0.05% NP-40, and 10% glycerol), and further purified by nickel chelate chromatography on a Ni-NTA (Qiagen) medium. Non-specifically bound proteins were removed from the protein bound medium by washing with 20 mM Tris-HCl buffer, pH 8, containing 25 mM imidazole, 500 mM NaCl, and 10% glycerol. After non-specifically bound proteins were removed from the medium the bound fusion protein was eluted with 20 mM Tris-HCl buffer, pH 8, containing 500 mM imidazole, 500 mM NaCl, and 10% glycerol.

Attempts were made to refold TGFβ$_1$-Thrombin using various refolding schemes which had previously been successful with renaturing other proteins.

Solubilizing the inclusion bodies in 2 M urea and 2 mM DTT (Method I) was effective in renaturing other proteins (IGF-1: Chang et al. In: *Protein Folding In Vivo and in Vitro*, ed. by Cleland, J. L., Symposium Series 526, American Chemical Society, Washington D.C., pp. 178–188, 1993, which is incorporated herein by reference) but did not produce an appreciable amount of biologically active TGFβ$_1$.

Refolding/reoxidation of TGFβ$_1$-Thrombin in the presence of glutathione and DTT as described by Glocker et al. (*J. Biol. Chem.* 91, 5868–5872, 1994; Method II, which is incorporated herein by reference) yielded a very small amount of renatured TGFβ$_1$ with little biological activity.

Method III, refolding the urea-solubilized aggregates from inclusion bodies at a protein concentration of 0.1 mg/ml in an optimized glutathione redox couple system (2 mM reduced: 0.2 mM oxidized) was determined to be the most effective method for renaturation of the isolated TGFβ.

Renaturation of the TGFβ$_1$ fusion protein (~13 kD) into soluble homodimers (~30 kD) was demonstrated by SDS-PAGE performed under non-reducing conditions.

Biological activity of the renatured recombinant TGFβ, fusion protein was confirmed by an Mv1Lu cell proliferation assay (Example 7) in which purified human platelet TGFβ₁ served as a positive control. Dialyzed protein fractions (5 to 30 μg/ml) from the glutathione redox-couple refolding system (Method III) exhibited an anti-proliferative activity comparable to the TGFβ₁ control treatments (50 to 200 pg/ml) in Mv1Lu cells. In contrast, fractions from Methods I and II, respectively, exhibited little or no biological activity. The inability of these fractions to inhibit Mv1Lu cell proliferation indicated that there was no effect of the final dialysis buffer components, at these dilutions, on Mv1Lu cell proliferation activity.

The biological activity of renatured TGFβ₁ in solution, and when it was adsorbed onto collagen- or fibronectin-coated surfaces was examined. In solution, renatured recombinant TGFβ₁ (by Method III) exhibited an anti-proliferative effect on Mv1Lu cells. Mv1Lu cells are highly efficient at adhesion and proliferation on collagen- or fibronectin-coated surfaces. TGFβ₁ adsorbed onto collagen and/or fibronectin exerts a similarly potent antiproliferative effect on Mv1Lu cells (~70% on collagen and ~40% on fibronectin) without affecting the ability of these cells to adhere to these surfaces.

EXAMPLE 6

Extraction, Purification and Renaturation of Biologically Active TGFβ Fusion Proteins in High Yield from *E. coli* Inclusion Bodies Frozen *E. coli* pellets, transformed with TGFβ₁-Thrombin or TGFβ₁-Thrombin-Collagen of induced cultures, prepared as described in Example 4, were suspended in 25 ml of lysis buffer (20 mM Tris, pH 8.0, 250 mM NaCl, 0.05% (v/v) NP-40, 0.4 mM PMSF, 25 μl β-mercaptoethanol, 10 mg lysozyme) at 4° C., and incubated at 4° C. for 30 minutes with constant stirring. The suspension was transferred to 50 ml centrifuge tubes and sonicated with a Polytron-sonicate, at a setting of #7 or 25,000 rpm (two cycles of 30 seconds) at 4° C. The sonicated lysate was then centrifuged at 12,000×g at 4° C. for 20 minutes. The supernatant was decanted and the pellet, which included inclusion bodies, were washed with Basic Binding buffer (20 mM Tris-HCl, pH 8.0, 250 mM NaCl, 0.05% (v/v) NP-40) at 4° C. and centrifuged at 12,000×g for 20 minutes.

The pellet, which included inclusion bodies, was suspended in 25 ml of denaturation buffer (8 M urea, 0.1 M sodium phosphate, 10 mM Tris, pH 8.0, made fresh daily by passing a stock 8 M urea solution (480 g/l of warm dH₂O) through a Mix-bed resin (TMD-8, Sigma) just before use and prior to the addition of the buffers. Seventeen μl of β-mercaptoethanol was added and the solution was vortexed vigorously until most of the pellet was dissolved.

The solution was then centrifuged at 20,000×g for 20 minutes at room temperature and the supernatant was collected.

About 5 μl of the supernatant was aliquoted into a microfuge tube, and 795 μl of water and 200 μl of BioRad Protein Assay Reagent was added, mixed well and the samples were read at 595 nm in a spectrophotometer using 5 μl of denaturation buffer, 790 μl of water and 200 μl of BioRad Protein Assay Reagent as a blank. The protein concentration was estimated from a protein standard curve.

The supernatant, which included the TGFβ fusion protein, was mixed with Ni-NTA resin (5 ml bed volume, equilibrated with denaturation buffer) in a 50 ml centrifuge tube and rocked for 1 hour at room temperature. The TGFβ fusion protein/resin mixture was loaded onto a 25 ml column, and the resin was allowed to settle and the liquid to drain off. The TGFβ fusion protein/resin was washed with 40 ml of denaturation buffer, pH 8.0.

The TGFβ fusion protein/resin was then washed with 30 ml of Ni-chelating column wash buffer A (denaturation buffer, adjusted to pH 6.5 with 2 M HCl, made fresh daily). The TGFβ fusion protein was eluted from the resin with Ni-chelating column Elution buffer B (denaturation buffer adjusted to pH 4.0 with 2 M HCl, made fresh daily). One ml fractions were collected. The protein concentration of 5 μl of each fraction was determined as described above.

Fractions with protein readings greater than 0.1 mg/ml were pooled. The volume was measured and the protein concentration of the pooled fractions was determined as described above.

The pooled fractions were diluted with denaturation buffer, pH 8.0 to a final protein concentration of <0.5 mg/ml (<0.1 mg/ml for TGFβ₁-Thrombin-Collagen constructs). The pooled samples were then further diluted with 4 volumes of freshly made Redox Buffer (20 mM Tris-HCl, pH 8.0, 250 mM NaCl, 0.05% (v/v) NP-40, 2 mM reduced glutathione, 0.2 mM oxidized glutathione) dropwise on ice with vigorous mixing.

The diluted protein was sealed in a container and stored overnight at 4° C. The diluted protein was then dialyzed against an equal volume of dialysis buffer (20 mM Tris, pH 8.0, 250 mM NaCl, 20% (v/v) glycerol) for 20 minutes. After 20 minutes, and every 20 minutes thereafter, the dialysis buffer was replaced with twice the volume of dialysis buffer previously used, until the volume of the dialysis buffer was 1 liter. The dialysis was then stored overnight at about 4° C. without stirring. The next morning the dialysis was stirred for 30 minutes. The dialysis buffer was replaced and the dialysis was stirred for 2 hours. The contents of the dialysis bag was collected, centrifuged at 5,000 rpm for 20 minutes at 4° C. and the supernatant was collected. The protein concentration of the collected supernatant was determined and the supernatant was stored at −70° C.

Induction of the TGFβ₁-Thrombin-Collagen fusion protein in the BL21(DE3) strain of *E. coli* yielded high levels of expression of the 12.5 kD polypeptide which was found in inclusion bodies. The inclusion bodies were solubilized in 8 M urea and purified by Ni-NTA metal chelate chromatography. Similar to the TGFβ₁-Thrombin fusion protein, pure TGFβ₁-Thrombin-Collagen protein was extracted, as demonstrated by a single 12.5 kD band on SDS-PAGE, in the presence of DTT. Upon oxidative refolding and dialysis, approximately 15 mg of pure soluble protein was obtained from a 250 ml bacterial culture.

To evaluate the kinetics of refolding, samples were taken at specific time intervals after the initiation of refolding and iodoacetamide (50 mM) was added immediately to block further reaction of the sulfhydryl groups. The samples were stored at 4° C. until analyzed by non-reducing SDS-PAGE. Dimers began to form after 2 hours of refolding, reaching maximal levels at 4 to 10 hours under the conditions described above.

Renaturation and assembly of the TGFβ₁-Thrombin-Collagen polypeptide (12.5 kD) into active soluble homodimers (25 kD) was demonstrated in the Mv1Lu cell proliferation assay in which commercially available purified human platelet TGFβ₁ served as a positive control. The TGFβ₁-Thrombin-Collagen fusion protein renatured from bacterial inclusion bodies by the glutathione redox refolding method exhibited an anti-proliferative activity comparable to the TGFβ₁ control treatments, although the specific activity of the recombinant growth factor preparation was considerably (~300 times) lower. Renatured TGFβ₁-Thrombin-Collagen fusion protein bound to collagen-coated wells also inhibited the proliferation of Mv1Lu cells. However, the level of inhibition observed for collagen-bound growth factor was much smaller than that observed when the unbound TGFβ₁-Thrombin-Collagen protein was added directly to the culture medium.

EXAMPLE 7

Bioassay for TGFβ Antiproliferative Effect on Mink Lung Epithelial-Like Cells (mv1lu)

Mink lung epithelial-like cells (Mv1Lu; American Type Culture Collection No. ATCC CCL64) were grown to a subconfluent density (80%) in DMEM (Gibco) with 10% (v/v) fetal calf serum (FCS). The medium also contained Gentamicin (50 μg/ml) and Fungizone (20 μg/ml). The cells were harvested by trypsinizing, in 0.25% (w/v) trypsin, 1 mM EDTA in Hanks BSS (Gibco/BRL) and plated in a 24 well flat-bottomed cell culture plates, with 100 to 150×10³ cells/well, in DMEM with 10% (v/v) FCS.

Positive control assays included human recombinant TGFβ in assay medium (0.1% (v/v) FCS in DMEM with 2 to 250 pg TGFβ/ml). Negative controls included no human recombinant TGFβ (0 TGFβ/ml) and dialysis buffer was added instead of TGFβ.

Samples were serially diluted into the assay medium. Cells were rinsed twice with DMEM and assay media was added (500 μl/well for controls and testing samples). The plates were incubated at 37° C. with 5% (v/v) $CO_2$ for 20 hours.

³H-Thymidine (ICN, Cat. # 2407005, 1 mCi/ml) uptake assays were performed by adding 20 μl/well (1 uCi) of ³H-thymidine and the incubation was continued for an additional 4 hours.

The media was removed and discarded. The wells were washed three times each for 10 minutes with 1.5 ml of cold 10% (w/v) trichloroacetic acid (TCA) and washed once with water. Five hundred μl of 0.2 M NaOH was added to each well and the samples were incubated at 37° C. for 1 hour. The samples were checked visually to determine if the cells were solubilized. If they were not, they were further incubated at 37° C. until solubilized.

At the end of the solubilization the samples were mixed gently and 200 μl of the contents of each well was added to a scintillation vial. An equal volume of 0.5 M acetic acid was then added to each sample and the samples were mixed. Scintillant (Ready Safe) was added to each of the samples and they were count for two minutes in a scintillation counter. After storage in the dark overnight the samples were again counted for 2 minutes.

EXAMPLE 8

Epithelialization of Collagen Gels with Human Keratinocyte Buttons

A TGFβ treated collagen carrier stem cell trap was prepared as follows: TGFβ₁ (20 ng/ml) and TGFβ₁-Thrombin-Collagen fusion protein (25 μg/ml) were reconstituted in DMEM and 200 μl of TGFβ₁ or TGFβ₁-Thrombin-Collagen was added to collagen carrier immobilized in 24 well cell culture plates. The samples were incubated for 2 hours at 22° C. At the end of the incubation, the wells which included the samples were rinsed twice with 1 ml each of DMEM. The DMEM medium also included Gentamicin (50 μg/ml) and Fungizone (20 μg/ml).

Dermal fibroblasts/mesenchymal cells were harvested as follows: Fresh human skin from surgery was collected and rinsed twice with sterile phosphate buffered saline (PBS) The adipose tissue was excised and the skin was cut into 4 mm×10 mm samples. The skin samples were incubated in prewarmed 0.5% (w/v) dispase/DMEM (10 ml for 2×2 cm² skin) at 37° C. for 90 minutes with agitation. At the end of the incubation, the keratinocyte layer was peeled off using fine forceps and stored on ice cold DMEM until required.

The dermis was incubated in collagenase-dispase solution (0.5% (w/v) dispase and 1,000 units/ml collagenase) in PBS for an additional 2 hours with agitation (10 ml for 2×2 cm² skin). At the end of the incubation, the collagenase/dispase was neutralized by the addition of FCS to a final concentration of 10% (v/v). The samples were then gently homogenized by drawing the mixture into a pipette and releasing it 20 times. The mixture was then filtered through a 100μ mesh filter and centrifuged to collect cells.

The cells were resuspended in 0.5% (v/v) FCS/DMEM and plated at 200×10³ cells/ml/well/collagen carrier. The plates were then incubated at 37° C. with 5% (v/v) $CO_2$ overnight.

At the end of the overnight incubation the medium was replaced with fresh 0.5% (v/v) FCS/DMEM. The plates were then incubated for an additional 1 to 3 days.

Keratinocyte buttons were prepared as follows: Fresh keratinocyte sheet from human skin was harvested, as described above. The keratinocyte sheet was cut into 2×2 mm² buttons. Medium was removed from each of the above described wells and the wells were rinsed once with DMEM. The keratinocyte buttons were implanted on the collagen carrier, immobilized with 3 μl of neutralized collagen (Vitrogen 1 mg/ml, neutralized with 10×PBS and 0.1 M NaOH, pH 7.2) and incubated at 37° C. for 30 minutes. At the end of the incubation, 1 ml of keratinocyte serum free medium (SFM, Gibco/BRL Cat# 17005-042) was added to each well and the samples were incubated at 37° C. with 5% (v/v) $CO_2$. The medium was replaced every 3 days.

Keratinocyte outgrowth assays were conducted as follows: The culture media was removed from the wells by suctioning, and the samples were fixed in 3% (v/v) paraformaldehyde/PBS for 30 minutes at 22° C. The fixative was then removed from each well and the samples were stained with 0.5% (w/v) Nile Blue Sulfate/1% (v/v) sulfuric acid/PBS for 1 hour at 37° C. The keratinocyte outgrowth was photographed with Polaroid 55 film.

EXAMPLE 9

Cell Proliferation and Matrix Binding Assays

The biological activity of solubilized recombinant TGFβ₁-Thrombin was tested in a series of cell proliferation assays as described by Ikeda et al. (*Biochemistry* 26, 2406–2410, 1987, which is incorporated herein by reference) using Mink Lung epithelial (Mv1Lu) cells with minor modifications.

Mv1Lu cells were maintained in log-phase growth in Dulbecco's modified Eagles medium (DMEM; GIBCO) supplemented with 1% penicillin/streptomycin and 10% (v/v) fetal calf serum (FCS; GIBCO) at 37° C., 5% (v/v) $CO_2$ in humidified air. For cell proliferation assays, cells were seeded in 24-well plates (Costar) at a density of 1.5×10⁵ cells/well in normal growth medium. After an overnight incubation, the medium was replaced with 0.1% v/v FCS/DMEM. Serially diluted, renatured recombinant TGFβ$_1$ fusion proteins were added to the wells and incubated for 24 hours. $^3$H-thymidine (1 μCi/well, specific activity 2 Ci/mmole, 74 GBq/mmole, ICN) was added during the last 4 hours of incubation. Human platelet-derived TGFβ$_1$ (R & D Systems) was used as a standard and as a control. After incubation, the cells were precipitated twice with cold 10% (w/v) trichloroacetic acid (TCA), extracted with 0.2 M NaOH, and neutralized with 0.5 M acetic acid for analysis by liquid scintillation counting in cocktail.

MvlLu cells were also used to assess the biological activity of the recombinant TGFβ$_1$-Thrombin fusion protein pre-absorbed onto collagen- and fibronectin-coated dishes. In these studies, 20 μl of pepsin-treated, acid-extracted bovine tendon collagen type I or human plasma fibronectin (20 μg/well; Telio) were dried onto each well of a 24-well plate (Costar) overnight. Following a brief ultraviolet light treatment to crosslink the matrix proteins, plates were counter-coated with 0.2% (w/v) bovine serum albumin (BSA). Serial dilutions of the recombinant TGFβ$_1$-Thrombin were added to the coated wells in PBS and incubated at 37° C. for 2 hours. The wells were rinsed 3 times with DMEM, and MvlLu cells (1.5×10$^5$ per well in 0.1% (v/v) FCS/DMEM) were added to each well. The cells were incubated for about 20 hours at 37° C., followed by quantification of $^3$H-thymidine incorporation into TCA-precipitable material as described above.

EXAMPLE 10

Collagen Binding Assay

Two different approaches were used to assess the affinity of the recombinant TGFβ$_1$-Thrombin-Collagen fusion protein for collagen and for gelatin.

In the first method, collagen and gelatin covalently conjugated to CNBr-activated Sephadex G-15 columns were used as test matrices. Preparations of native and denatured purified rat tail type I collagen were coupled onto CNBr-activated Sephadex G-15 beads. The beads were then washed extensively with 50 mM Tris buffer, pH 8, containing 1 M NaCl. The fusion protein was applied to the medium in a buffered saline solution and was eluted with a linear salt gradient from 0.2 to 1 M NaCl.

In the second method, the recombinant fusion protein was first immobilized onto Ni-NTA medium, then collagen (biosynthetically labeled with $^3$H-proline and purified from human fibroblast cultures) was applied to the Ni-NTA medium, and eluted with a linear gradient of either phosphate buffered NaCl (0.15 to 1.5 M) or urea (0 to 4 M).

Virtually, all of the recombinant growth factor bound to the collagen G-15 under these conditions, as determined by protein assays. Attempts to elute the bound protein from the collagen medium with a salt gradient or 2 M urea were ineffective, suggesting that TGFβ$_1$-Thrombin-Collagen associates tightly with collagen. Similar results were obtained when TGFβ$_1$-Thrombin-Collagen was bound to a gelatin-Sephadex medium.

A different strategy was attempted in which the TGFβ$_1$-Thrombin-Collagen fusion protein was first immobilized on Ni-NTA medium and then exposed to biosynthetically-labeled $^3$H-collagen, which was loaded subsequently onto the medium. Under these conditions, a large portion of the radioactivity was found to bind to the medium. Washing the medium with a linear gradient of NaCl from 0.15 to 1.5 M did not release the $^3$H-collagen. However, application of a urea gradient (0 to 4.0 M) was able to quantitatively elute all bound radioactivity. In contrast, when the TGFβ$_1$-Thrombin fusion protein, comprising the (His)$_6$ tag and the TGFβ$_1$ active fragment, was applied to the Ni-NTA medium under identical conditions, very little $^3$H-collagen was retained on the medium, suggesting that the auxiliary collagen binding domain in TGFβ$_1$-Thrombin-Collagen afforded this high affinity interaction.

EXAMPLE 11

Stimulation of the Proliferation of NIH-3T3 Mouse Fibroblasts

The ability of TGFβ$_1$-Thrombin and TGFβ$_1$-Thrombin-Collagen to stimulate the proliferation of NIH-3T3 mouse fibroblasts was assayed by plating NIH-3T3 mouse fibroblasts in 24 well plates at subconfluent densities (1.5×10$^5$ cells/well) and culturing the cells for 48 hours in DMEM containing 0.5% (v/v) fetal calf serum. Commercial TGFβ$_1$ or renatured TGFβ$_1$-Thrombin-Collagen samples were then added to each well and incubated for 18 hours prior to the addition of $^3$H-thymidine, followed by an additional 4 hours of incubation. To evaluate the effect of collagen-bound TGFβ$_1$-Thrombin-Collagen on the 3T3 fibroblasts, the fusion protein was first bound to collagen-coated wells. Cells (1.5×10$^5$ cells/well) were seeded on top of the collagen with DMEM containing 0.5% (v/v) fetal calf serum or 0.5% (w/v) ITS (insulin, transferrin and selenium from Collaborative Biomedical Products, Mass.), harvested by trypsinization 72 hours later and quantified by direct counting.

As observed with human platelet TGFβ$_1$, TGFβ$_1$-Thrombin-Collagen treatment of 3T3 fibroblasts for 18 hours following a 48-hour low serum starvation, resulted in a 30-fold increase in $^3$H-thymidine incorporation. When TGFβ$_1$-Thrombin-Collagen was applied and bound to collagen-coated culture wells, and then cells were seeded on top of the TGFβ$_1$-Thrombin-Collagen/collagen in 0.5% (v/v) fetal calf serum/DMEM or ITS, no significant amount of stimulation of cell proliferation was observed, suggesting that the tight binding of TGFβ$_1$-Thrombin-Collagen to collagen lowered the availability and/or the rate if release of the biologically active growth factor. By contrast, commercial TGFβ$_1$ absorbed onto collagen-coated wells stimulated the proliferation of 3T3 cells approximately fifteen fold.

EXAMPLE 12

Evaluation of TGFβ/Collagen Matrices in Wound Healing Models

The function of the fusion TGFβ were assessed in a series of classic bone healing models. Comparative studies utilizing the rat calvarial defect model in which a collagen matrix is used in the presence or absence of adsorbed TGFβ fusion proteins. The rate and extent of bone healing were evaluated by radiological and histological methods.

TGFβ$_1$ fusion protein was found to have a profound effect on bone healing in the rat calvarial defect model. The results demonstrated a marked stimulation of wound closure and osteogenesis at 2 and 4 weeks after surgery. In control rats, scar tissue formation was observed, whereas in the TGFβ$_1$ treated rats bone formation, rather than scar tissue was observed.

Histological examination of the tissue showed a marked recruitment of osteogenic precursors, a characteristic profile of cellular maturation and effective absorption of the original collagen matrix. By contrast, the collagen matrix alone (control) produced granulation tissue characterized by an infiltration of inflammatory cells. Quantification of calcium deposition in control versus TGFβ impregnated collagen matrices revealed significant improvements which were evident within 2 weeks. Angiogenesis was evident with TGFβ/collagen, as was a remarkable absence of adhesions between the newly formed bone and the underlying dura mater.

EXAMPLE 13

Development and Characterization of a Mesenchymal Stem Cell Trap

A diagram of wound healing stages observed within TGFβ treated collagen matrices depicts three major features: (I) recruitment and expansion of a mesenchymal stem cell (MSC) population, (II) elaboration (of factors) and differentiation of cellular phenotype, and (III) resolution and remodeling of the extracellular matrix (see FIG. 1).

Based on the magnitude and extent of precursor cell migration and proliferation observed in the rat calvarial model (Stage I), TGFβ impregnated collagen matrices were tested for their ability to selectively reinforce the proliferation of mesenchymal stem cells that are present in low abundance within human bone marrow aspirates under conditions that the remainder of the cellular components of the marrow would not survive.

Rescue and selection of TGFβ responsive stem cells from human bone marrow aspirates upon 15 days of serum deprivation was observed.

EXAMPLE 14

2-Stage Histogenesis of Human "Artificial Skin" on Collagen Supports

Collagen matrices and sheets, though optimal in terms of structural integrity and biodegradability, can cause inflammatory responses (rejection) and fibrosis (scarring). By contrast, TGFβ impregnated collagen matrices inhibit inflammatory processes while promoting angiogenesis and histogenesis. TGFβ is a natural and critical component regulating epithelial-mesenchymal interactions in the developmental morphogenesis of skin appendages. Collagen bound TGFβ$_1$-Thrombin-Collagen fusion proteins can function effectively to select and expand (capture) a population of mesenchymal stem cells in vitro.

The development of an autologous "artificial" skin is feasible. The experimental procedure is to select and expand a population of explanted human fibroblasts, along with other resident mesenchymal precursors, within TGFβ impregnated collagen sheets. This procedure is continued in vitro up to an optimized point whereby the collagen sheet is effectively cellularized yet not degraded. At or just prior to this point, the collagen/connective tissue sheet is epithelialized by the application of an explanted plug of keratinocytes.

The human artificial skin comprised of TGFβ impregnated collagen sheets which have been cellularized and epithelialized in a 2-Stage approach is evaluated histologically and, once experimental conditions have been optimized, the "skin" is tested in a nude mouse wound healing model.

In these animal models, several considerations and critical parameters will be evaluated, as follows: Comparative studies are performed to evaluate the outcome and scar formation involving TGFβ/collagen sheets cultured under high serum conditions (mostly fibroblastic cells) versus TGFβ/ collagen sheets in which the population of pluripotent mesenchymal stem cells have been selected and expanded by culture under low serum conditions.

Such studies are expected to result in an enrichment (recruitment and expansion) of pluripotent stem cells which will facilitate normal histogenesis and wound healing. The application of recombinant TGFβ fusion proteins, including collagen-binding and fibronectin-binding constructs, to the cellularized "skin" (i.e., cellularized/epithelialized collagen sheets) and/or the wound surface is evaluated in terms of efficacy in promoting adherence, angiogenesis, and histogenesis. Such studies are also expected to result in a secondary application of TGFβ fusion proteins which will retard rejection and promote fusion of cultured tissues. The timing of each stage of the ex vivo tissue culture, as well as the thickness and physicochemistry of the collagen sheets, is also assessed.

EXAMPLE 15

The Use of TGFβ as a Wound Healing Enhancing Agent

TGFβ is known to effect wound healing by modulating stem cells proliferation and the expression of specific genes including those encoding for extracellular matrix proteins and cellular receptors. Numerous studies using animal models have demonstrated the potential of TGFβ to promote wound healing. TGFβ of the present invention exhibits biological activity and its use, in place of the naturally occurring TGFβ, allows the treatment of many conditions which had previously been considered as only potential clinical applications, due to the limited availability of TGFβ. Regeneration of the Skeleton:

It has been found that injections of TGFβ$_1$ on the periosteal layer stimulated bone formation in newborn rats. Different dosages of TGFβ added to demineralized bone matrix paste, formed into cylinders and implanted onto the periosteum of rabbits have shown that TGFβ induced higher levels of (accelerated) trabecular bone formation than controls. TGFβ also caused greater resorption of the demineralized bone. It has also been shown that a single application of TGFβ$_1$ in a simple 3% (w/v) methylcellulose gel to large skull defects in rabbits was able to induce intramembranous bone formation and complete bony bridging of defects was observed within 28 days after treatment with 2 μg of TGFβ$_1$. In neonatal rats, 12-day treatment of TGFβ$_1$ injection onto the outer periostea of the right side of the parietal bone increased the number of osteoprogenitor cells, resulting in intramembranous ossification. In adult rats, TGFβ$_1$ induced differentiation of chondrocytes. Cartilage masses were found to be surrounded by mesenchymal cells. In these animals the cartilage matrix was partially calcified, with chondrocytes buried therein. Marrow cavities containing some multinuclear osteoblasts were also observed in the calcified matrix. These findings indicate that TGFβ$_1$ stimulated the differentiation of mesenchymal cells into chondrocytes and produced cartilaginous matrix. TGFβ$_1$ induced intramembranous ossification of the parietal bone in neonatal rats, and it induced endochondral ossification in adults. These results show different responses of mesenchymal cells in the periosteum to TGFβ$_1$ which may depend on the age of the animals used; namely, they may reflect the respective osteogenic stages of modeling and remodeling.

It has also been shown that: TGFβ counteracts the deleterious effects of interleukin-1 (IL-1) on articular cartilage proteoglycan synthesis and content indicating that TGFβ plays an important role in articular cartilage restoration after IL-1 induced proteoglycan depletion; short term systemic injection of recombinant $TGF\beta_2$ increases cancellous bone formation rate in juvenile and adult rats; continuous local application of TGFβ for 6 weeks enhances fracture healing of tibial defects in rabbits; and local injection of TGFβ at the site of tibial fractures induced a dose-dependent increase in the cross-sectional area of the callus and bone at the fracture line.

Skin Wound Healing:

The treatment of incisional wounds of rats, which received total body radiation, with a single dose of $TGF\beta_1$ (2 μg/wound) using 3% (w/v) methylcellulose as a delivery vehicle, resulted in a significant acceleration of soft tissue repair and wound-breaking strength in the absence of monocytes and macrophages. $TGF\beta_1$ was not able to reverse healing deficit in the megavoltage electron beam surface irradiated skin wounds. The topical treatment of partial-thickness wounds in pigs with TGFβ using Silvadene cream (Marion Labs, Kansas, Mo.) as a vehicle was shown to accelerate the regeneration of dermis. It has also been shown that TGFβ accelerated the maturation of a neo-vascularized skin flap in rabbits.

Protection and Rescue From Impaired Wound Healing:

It has been shown that: mice which received TGFβ prior to treatment of high doses of 5-fluro-uracil exhibited a hematological recovery and were preferentially rescued by a suboptimal number of transplanted bone marrow cells; pretreatment of mice with TGFβ protected 70–80% of them from lethal doses of the noncycle active chemotherapeutic drug, doxorubicin hydrochloride (DXR); and parenteral steroids (β-methasone, 12 mg/50 g injected intramuscularly twice daily) induced an impairment of breaking load on a healed longitudinal intestinal wound in pigs. Also, TGFβ in a collagen suspension was used to treat these wounds and was found to reverse the effect of the steroids and significantly strengthened these wounds.

Other studies have been directed at the effect of TGFβ on an adriamycin-impaired wound healing model. In this model, a systemic adriamycin injection (8 mg/kg) produces significant decreases in wound tear strength and wound tear energy when compared with that of normal rats at 7 and 10 days. A single dose of TGFβ (2 μg) in a collagen vehicle was shown to stimulate a reversal of this wound healing impairment at day 10. Similarly, intravenously administered TGFβ at 100–500 mg/kg dosage can reverse age- or glucocorticoid-impaired healing of incisional wounds. Treatment of experimental allergic encephalomyelitis (EAE) with $TGF\beta_2$ resulted in the inhibition of T-cell activation and proliferation in vitro. Long-term treatment was effective in reducing clinical severity of EAE suggesting a potential use of $TGF\beta_2$ as a therapeutic agent for human demyelinating diseases such as multiple sclerosis.

Protection Against Myocardial Dysfunction and Stroke:

It has been shown that TGFα reduces endothelial cell release of nitric oxide, while TGFβ appears to protect against myocardial dysfunction induced by prolonged ischemia and reperfusion probably by reducing plasma TGFα levels, blocking neutrophil adherence, and promoting nitric oxide release.

Other studies have been directed at the effect of TGFβ on thromboembolic stroke in a rabbit model. An autologous clot embolus was introduced intracranially through the right internal carotid artery of rabbits to induce a thromboembolic stroke. TGFβ in an albumin vehicle was administered as an intracarotid bolus immediately before autologous clot embolization. The results showed treatment with 10 and 50 μg TGFβ reduced the infarct size and there was a greater return of cerebral blood flow in the first 2 hours after embolization.

Other studies have addressed the ability of TGFβ to preserve endothelial functions of coronary arteries in dogs by infusing TGFβ into the left anterior descending coronary artery distal to the site subjected to multiple brief occlusions and reperfusion. $TGF\beta_1$ prevented impaired endothelium-dependent relaxation after multiple brief occlusions and reperfussions suggesting that $TGF\beta_1$ can play a protective role in the endothelial injury induced by repeated episodes of coronary artery occlusion and reperfusion.

Immune Suppression:

It has also been shown that prolonged survival of cardiac graft transplants can be achieved by injecting plasmid DNA encoding TGFβ under the control of SV40 promoter into grafts from syngeneic or allogenic donors prior to implantation into recipients. In other studies in mice, the intramuscular injection of a vector encoding $TGF\beta_1$ depressed the anti-transferrin antibody response and caused an 8-fold increase in plasma $TGF\beta_1$ activity. The $TGF\beta_1$ plasmid injection induced biological effects characteristic of TGFβ in regulating humoral and cellular immune responses in vivo but did not cause muscle infiltration with monocytes or neutrophils and there was no evidence for fibrotic changes.

Applications for Humans Currently Under Clinical Trials:

Other studies have shown in a randomized multicenter clinical study of patients with full-thickness macular holes, that 0.66 pg of $TGF\beta_2$, applied locally, to be successful in flattening the rim of subretinal fluid surrounding macular holes. The study further showed that $TGF\beta_2$ retreatment (1.33 pg) on full-thickness macular holes which failed to close after vitreous surgery appeared to have a beneficial effect on both neurosensory retinal flattening and visual outcome.

Pharmacokinetics of TGFβ:

Other studies have included a detailed pharmacokinetic and tissue distribution study of TGFβ as a potential intravenous bolus or topical wound healing enhancing agent It has been found that the half-life of topically administered TGFβ has a plasma half-life ranging between 61 to 163 minutes depending on the dose and duration of the treatment. Other studies have shown that $^{125}$I-TGFβ was detectable 16 days after a single dose of TGF, formulated in a 3% (w/v) methylcellulose vehicle, in the rabbit calvarial defect model. It has also been demonstrated that high-dose dermal application of TGFβ resulted in local effects attributed to known biological activities of TGFβ at the wound sites without systemic toxicity.

EXAMPLE 16

Methods of Delivery of TGF-β

Systemic Injection:

A suitable method to administer TGFβ is injection of the growth factor in a liquid vehicle.

Injection of DNA Vector:

Plasmid DNA encoding the human $TGF\beta_1$ under the control of a known promoter can be injected intramuscularly.

Topical Application:

Silvadene cream (3% (w/v) methylcellulose) and soluble collagen are useful as vehicles in topical or local administration of TGFβ.

Implantable Solid Phase Carriers:

TGFβ (1 to 10 μg) enclosed in a gelatin capsule containing methylcellulose can be implanted into surgical chambers and in bone to increased bone formation. Biodegradable controlled release systems for $TGF\beta_1$ which comprise poly (DL-lactic-co-glycolic acid) (PLPG) and demineralized bone matrix (DBM) can be used. DBM alone, 3% (w/v)

methylcellulose gel, and alginate beads are also effective carriers for TGFβ.

EXAMPLE 17

Preparation of a BMP Fusion Protein

A cDNA of human BMP-3 was obtained from Dr. Hari Reddi. The cDNA sequence encoding the C-terminal 183 amino acids of human BMP-3 was ligated in frame to pET28 vector (Novagen), and maintained in the XL Blue strain of E. coli BL21(DE3). The orientation and reading frame of the insert was confirmed by DNA sequence analysis.

The pET-BMP-3 construct was transformed into E. coli BL21(DE3), and high level expression of recombinant proteins was induced in the presence of 0.4 mM isopropyl thiogalactopyranoside (IPTG) for 5 hours at 37° C. with shaking at 300 rpm.

The construct contained a $(His)_6$ leader sequence at the N-terminus of the fusion protein, a thrombin cleavage site in the first proteinase site, followed by a collagen binding site and a truncated active BMP-3 fragment (i.e. the plasmid encoded SEQ ID NOs. 22:14:19:37).

EXAMPLE 18

Extraction, Purification and Renaturation of Biologically Active BMP-3 Fusion Proteins in High Yield from E. coli Inclusion Bodies BMP-3 fusion protein was prepared from E. coli transformed with the construct described in Example 17 by the method described in Example 6 by isolation of inclusion bodies from induced E. coli. The BMP-3 fusion protein was then purified by Ni-chelate chromatography. After purification one band was observed when analyzed by reducing SDS gel electrophoresis.

Oxidative renaturation of the BMP-3 fusion protein was conducted using the controlled glutathione redox system as described in Example 6 except the protein concentration was 0.4 mg/ml, the refolding temperature was 4° C. and an additional dialysis was included for storage of the refolded protein, as follows: the refolded protein was dialyzed against 20% (v/v) acetonitrile, 0.01% (v/v) trifluroacetic acid. The 20% (v/v) acetonitrile, 0.01% (v/v) trifluroacetic acid solution was changed three times at 20 minute intervals. The dialyzed protein was then removed from the dialysis tubing, lyophilized and stored at 4° C. until required. The lyophilized protein was reconstituted with 0.1% (w/v) BSA, 0.01 M HCl before use.

Briefly the renaturation was performed as follows: Purified BMP-3 fusion protein was diluted with denaturation buffer, pH 8.0 to a final protein concentration of <0.4 mg/ml. The BMP-3 fusion protein was then further diluted with 4 volumes of freshly made Redox Buffer (20 mM Tris-HCl, pH 8.0, 250 mM NaCl, 0.05% (v/v) NP-40, 2 mM reduced glutathione, 0.2 mM oxidized glutathione) dropwise on ice with vigorous mixing.

The diluted protein was sealed in a container and stored overnight at 4° C. The diluted protein was then dialyzed against an equal volume of dialysis buffer (20 mM Tris, pH 8.0, 250 mM NaCl, 20% (v/v) glycerol) for 20 minutes. After 20 minutes, and every 20 minutes thereafter, the dialysis buffer was replaced with twice the volume of dialysis buffer previously used, until the volume of the dialysis buffer was 1 liter. The dialysis was then stored overnight at about 4° C. without stirring. The next morning the dialysis was stirred for 30 minutes. The dialysis buffer was replaced and the dialysis was stirred for 2 hours. The contents of the dialysis bag was collected, centrifuged at 5,000 rpm for 20 minutes at 4° C. and the supernatant was collected. The protein concentration of the collected supernatant was determined and the supernatant was stored at −70° C.

For long term storage, BMP protein solutions were dialyzed into 20% (v/v) acetonitrile, 0.01% (v/v) trifluroacetic acid. The 20% (v/v) acetonitrile, 0.01% (v/v) trifluroacetic acid solution was changed three times at 20 minute intervals. The dialyzed protein was then removed from the dialysis tubing, lyophilized and stored at 4° C. until required. The lyophilized protein was reconstituted with 0.1% (w/v) BSA, 0.01 M HCl before use.

Samples of the renatured BMP-3 fusion protein were analyzed by non-reducing SDS gel electrophoresis showed that at zero time all the BMP-3 fusion protein was present as a monomer and that after 24 hours of the renaturation treatment approximately 30% of the protein was present as a dimer.

EXAMPLE 19

In Vitro Bioassay for Renatured BMP-3 Fusion Protein

A bioassay for the renatured BMP-3 fusion protein was performed using an osteoblastic cell line (SaOS-2 obtained from ATCC). Osteoponin was monitored in response to BMP-3 added to the cells. This assay was developed to allow monitoring of biological activity of BMP-3 in vitro. Prior to the development of this assay, there was no in vitro assay for BMP-3 and time consuming in vivo assays, such as that described in Example 20, were required.

SaOS-2 cells were maintained in 10% (v/v) fetal bovine serum/McCoy 5A medium. Cells were plated into 24-well tissue culture plates in 10% (v/v) fetal bovine serum/McCoy 5A medium and allowed to attach overnight. The medium was removed and replaced with assay medium (0.5% (v/v) fetal bovine serum/McCoy 5A medium). BMP-3 was added to the cell culture at a concentration of from 1 ng to 100 ng. Cells were incubated at 37° C. in the assay medium for 5 days. At the end of the incubation, cells were washed extensively (3 times) with PBS and then 200 ml cell lysis buffer (50 mM Tris, pH 7.5, 150 mM NaCl, 2 mM EDTA, 0.1 mM PMSF, 5 mg/ml Leupetin and 0.2% (v/v) Triton X-100) was added to the cells. The cells were lysed on ice for 10 minutes and the lysate was collected. A 10 ml aliquot of the lysate was taken and assayed for protein content (using BioRad protein assay reagent). Cellular proteins were separated using 8 to 16% (w/v) gradient PAGE-SDS gels, and transferred to nitrocellulose membranes (0.45 mm pore size obtained from Millipore) using a semi-dry transfer unit (Hoefer Scientific Instruments). Non-specific binding sites on the nitrocellulose membranes, which remained after the transfer, were blocked with 5% (v/v) milk in a solution of PBS/0.1% (v/v) Tween-20 for 1 hour.

The first osteopotin antiserum used was provided by Dr. Fisher of the NIH (L123 anti human osteopotin antibody). Antibodies were diluted 1:1000 in PBS/0.1% (v/v) Tween-20. Alkaline phosphatase conjugated goat anti-rabbit serum IgG was used as a secondary antibody. Immunoreactive proteins were visualized by adding 5-bromo-4-chloro-indolyl phosphate (BCIP) and nitro blue tetrazolum (TLC) solutions according to the manufacture's instructions.

Two novel bands with molecular weights of about 46,000 and 26,000 were induced by the added, renatured BMP-3.

Other growth/differentiation factors, TGFβ$_1$, TGFβ$_2$ and BMP-2, did not induce these two bands. The density of the 26,000 band increased proportionally with the dose of BMP-3 added to the cells. The results indicate that BMP-3 was capable of inducing specific proteins within the osteoblastic cells and that the induction was proportional to the amount of BMP-3 added.

EXAMPLE 20

In Vivo Bioassay for Renatured BMP-3 Fusion Protein

BMP-3 fusion protein was assayed in vivo in a rat subcutaneous implantation assay.

Type I collagen sponges were derived from pepsin treated bovine tendons by the method of Nimni et al (*J. Biomedical Materials Res.* 21 741–771, 1987). BMP-3 fusion protein, which included a collagen binding domain, was bound to the collagen of the collagen sponges by adding 0.01 ml of renatured BMP-3 to a 4 mm diameter×2 mm thick sponge. The BMP-3-sponges were implanted subcutaneously in rats.

After two weeks the BMP-3-sponges were retrieved and analyzed. Von-Kossa staining revealed that BMP-3 treated sponges showed a significant amount of calcium deposits. In control sponges, sponges which were not treated with the BMP-3 fusion protein, no calcium deposits were observed.

The results indicate that the BMP-3 fusion protein exhibit marked osteogenetic activity.

The present invention is not to be limited to the specific embodiments which are shown or described above and which are merely illustrative. Various and numerous other arrangements and applications may be devised by one skilled in the art without departing from the spirit and scope of this invention. For example, one skilled in the art will be aware that the DNA sequences can be changed without changing the amino acid sequence of the proteins encoded or that the DNA can be changed to change the amino acid specified at a particular place in a polypeptide, but which do not change the functional properties of the polypeptide produced from the DNA sequence, i.e. conservative substitutions. Such modified DNA sequences and amino acid sequences are considered to be included within the scope of the present invention.

The scope of the invention is defined in the following claims.

What is claimed is:

1. A method of enhancing bone growth in a mammal comprising: impregnating a matrix with bone morphogenetic fusion protein; and implanting the impregnated matrix, in the mammal, at the site where bone growth is required, wherein the bone morphogenetic fusion protein includes therein: (i) a bone growth enhancing fragment present in the mature form of a bone morphogenetic protein selected from the group consisting of BMP-2, BMP-3, BMP-4, BMP-5, BMP-7, BMP-8, and BMP-10; and (ii) a purification tag that is $(His)_6$, to enhance bone growth in the mammal.

2. A method of enhancing bone growth in a mammal comprising: impregnating a matrix with bone morphogenetic fusion protein; and implanting the impregnated matrix, in the mammal, at the site where bone growth is required, wherein the bone morphogenetic fusion protein includes therein: (i) the amino acid sequence of a bone growth enhancing fragment present in the mature form of a bone morphogenetic protein that is BMP-3; and (ii) a purification tag that is $(His)_6$, to enhance bone growth in the mammal.

* * * * *

```
                        SEQUENCE LISTING

<160> NUMBER OF SEQ ID NOS: 51

<210> SEQ ID NO 1
<211> LENGTH: 5
<212> TYPE: PRT
<213> ORGANISM: Human

<400> SEQUENCE: 1

His Asp Val Leu Lys
1               5

<210> SEQ ID NO 2
<211> LENGTH: 4
<212> TYPE: PRT
<213> ORGANISM: Human

<400> SEQUENCE: 2

Leu Leu Val Tyr
1

<210> SEQ ID NO 3
<211> LENGTH: 4
<212> TYPE: PRT
<213> ORGANISM: Human

<400> SEQUENCE: 3

Ala Ala Pro Phe
1

<210> SEQ ID NO 4
<211> LENGTH: 3
<212> TYPE: PRT
<213> ORGANISM: Human

<400> SEQUENCE: 4

Ala Pro Ala
1
```

```
<210> SEQ ID NO 5
<211> LENGTH: 3
<212> TYPE: PRT
<213> ORGANISM: Human

<400> SEQUENCE: 5

Ala Ala Ala
 1

<210> SEQ ID NO 6
<211> LENGTH: 2
<212> TYPE: PRT
<213> ORGANISM: Human

<400> SEQUENCE: 6

Gly Arg
 1

<210> SEQ ID NO 7
<211> LENGTH: 3
<212> TYPE: PRT
<213> ORGANISM: Human

<400> SEQUENCE: 7

Leu Thr Arg
 1

<210> SEQ ID NO 8
<211> LENGTH: 7
<212> TYPE: PRT
<213> ORGANISM: Human

<400> SEQUENCE: 8

Pro Ile Glu Phe Phe Arg Leu
 1               5

<210> SEQ ID NO 9
<211> LENGTH: 7
<212> TYPE: PRT
<213> ORGANISM: Human

<400> SEQUENCE: 9

Lys Pro Ala Lys Phe Phe Arg
 1               5

<210> SEQ ID NO 10
<211> LENGTH: 6
<212> TYPE: PRT
<213> ORGANISM: Human

<400> SEQUENCE: 10

Leu Ser Phe Leu Ala Leu
 1               5

<210> SEQ ID NO 11
<211> LENGTH: 3
<212> TYPE: PRT
<213> ORGANISM: Human

<400> SEQUENCE: 11

Ala Ala Phe
 1

<210> SEQ ID NO 12
```

```
<211> LENGTH: 12
<212> TYPE: DNA
<213> ORGANISM: Human
<220> FEATURE:
<221> NAME/KEY: CDS
<222> LOCATION: (1)...(12)

<400> SEQUENCE: 12 atc gaa ggt cgt                                                        12
Ile Glu Gly Arg
  1

<210> SEQ ID NO 13
<211> LENGTH: 4
<212> TYPE: PRT
<213> ORGANISM: Human

<400> SEQUENCE: 13

Ile Glu Gly Arg
  1

<210> SEQ ID NO 14
<211> LENGTH: 18
<212> TYPE: DNA
<213> ORGANISM: Human
<220> FEATURE:
<221> NAME/KEY: CDS
<222> LOCATION: (1)...(18)

<400> SEQUENCE: 14 ctg gtt ccg cgt gga tcc                                                18
Leu Val Pro Arg Gly Ser
  1               5

<210> SEQ ID NO 15
<211> LENGTH: 6
<212> TYPE: PRT
<213> ORGANISM: Human

<400> SEQUENCE: 15

Leu Val Pro Arg Gly Ser
  1               5

<210> SEQ ID NO 16
<211> LENGTH: 3
<212> TYPE: PRT
<213> ORGANISM: Human

<400> SEQUENCE: 16

Arg Gly Asp
  1

<210> SEQ ID NO 17
<211> LENGTH: 18
<212> TYPE: DNA
<213> ORGANISM: Human
<220> FEATURE:
<221> NAME/KEY: CDS
<222> LOCATION: (1)...(18)

<400> SEQUENCE: 17 ggt ggc tgg agc cac tgg                                                18
Gly Gly Trp Ser His Trp
  1               5

<210> SEQ ID NO 18
<211> LENGTH: 6
```

```
<212> TYPE: PRT
<213> ORGANISM: Human

<400> SEQUENCE: 18

Gly Gly Trp Ser His Trp
 1               5

<210> SEQ ID NO 19
<211> LENGTH: 27
<212> TYPE: DNA
<213> ORGANISM: Human
<220> FEATURE:
<221> NAME/KEY: CDS
<222> LOCATION: (1)...(27)

<400> SEQUENCE: 19 tgg cgc gaa ccg agc ttc atg gct ctg                           27
Trp Arg Glu Pro Ser Phe Met Ala Leu
 1               5

<210> SEQ ID NO 20
<211> LENGTH: 9
<212> TYPE: PRT
<213> ORGANISM: Human

<400> SEQUENCE: 20

Trp Arg Glu Pro Ser Phe Met Ala Leu
 1               5

<210> SEQ ID NO 21
<211> LENGTH: 18
<212> TYPE: DNA
<213> ORGANISM: Human
<220> FEATURE:
<221> NAME/KEY: CDS
<222> LOCATION: (1)...(18)

<400> SEQUENCE: 21 cat cat cat cat cat cac                                       18
His His His His His His
 1               5

<210> SEQ ID NO 22
<211> LENGTH: 6
<212> TYPE: PRT
<213> ORGANISM: Human

<400> SEQUENCE: 22

His His His His His His
 1               5

<210> SEQ ID NO 23
<211> LENGTH: 45
<212> TYPE: DNA
<213> ORGANISM: Human
<220> FEATURE:
<221> NAME/KEY: CDS
<222> LOCATION: (1)...(45)

<400> SEQUENCE: 23 aaa gaa acc gct gct gct aaa ttc gaa cgc cag cac atg gac agc   45
Lys Glu Thr Ala Ala Ala Lys Phe Glu Arg Gln His Met Asp Ser
 1               5                  10                  15

<210> SEQ ID NO 24
<211> LENGTH: 15
<212> TYPE: PRT
```

```
<213> ORGANISM: Human

<400> SEQUENCE: 24

Lys Glu Thr Ala Ala Ala Lys Phe Glu Arg Gln His Met Asp Ser
 1               5                  10                  15

<210> SEQ ID NO 25
<211> LENGTH: 654
<212> TYPE: DNA
<213> ORGANISM: Human
<220> FEATURE:
<221> NAME/KEY: CDS
<222> LOCATION: (1)...(654)

<400> SEQUENCE: 25 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
 1               5                  10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
            35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
        50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
                100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
            115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
        130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc     624
Leu Lys Ser Ser Lys Tyr Ile Ala Trp Pro Leu Gln Gly Trp Gln Ala
        195                 200                 205 acg ttt ggt ggt ggc gac cat cct cca aaa                             654
Thr Phe Gly Gly Gly Asp His Pro Pro Lys
        210                 215

<210> SEQ ID NO 26
<211> LENGTH: 218
<212> TYPE: PRT
<213> ORGANISM: Human
```

-continued

```
<400> SEQUENCE: 26

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys
    210                 215

<210> SEQ ID NO 27
<211> LENGTH: 27
<212> TYPE: DNA
<213> ORGANISM: Human
<220> FEATURE:
<221> NAME/KEY: CDS
<222> LOCATION: (1)...(27)

<400> SEQUENCE: 27 tac cca tac gat gtt cca gat tac gct                              27
Tyr Pro Tyr Asp Val Pro Asp Tyr Ala
 1               5

<210> SEQ ID NO 28
<211> LENGTH: 9
<212> TYPE: PRT
<213> ORGANISM: Human

<400> SEQUENCE: 28

Tyr Pro Tyr Asp Val Pro Asp Tyr Ala
 1               5

<210> SEQ ID NO 29
<211> LENGTH: 337
<212> TYPE: DNA
<213> ORGANISM: Human
<220> FEATURE:
<221> NAME/KEY: CDS
<222> LOCATION: (1)...(336)
```

-continued

<400> SEQUENCE: 29

```
gcc ctg gac acc aac tat tgc ttc agc tcc acg gag aag aac tgc tgc    48
Ala Leu Asp Thr Asn Tyr Cys Phe Ser Ser Thr Glu Lys Asn Cys Cys
 1               5                  10                  15 gtg cgg cag ctg tac att gac ttc cgc aag gac ctc ggc tgg aag tgg    96
Val Arg Gln Leu Tyr Ile Asp Phe Arg Lys Asp Leu Gly Trp Lys Trp
             20                  25                  30 atc cat gag ccc aag ggc tac cat gcc aac ttc tgc ctc ggg ccc tgc   144
Ile His Glu Pro Lys Gly Tyr His Ala Asn Phe Cys Leu Gly Pro Cys
         35                  40                  45 ccc tac att tgg agc ctg gac acg cag tac agc aag gtc ctg gcc ctg   192
Pro Tyr Ile Trp Ser Leu Asp Thr Gln Tyr Ser Lys Val Leu Ala Leu
     50                  55                  60 tac aac cag cat aac ccg ggc gcc tcg gcg gcg ccg tgc tgc gtg ccg   240
Tyr Asn Gln His Asn Pro Gly Ala Ser Ala Ala Pro Cys Cys Val Pro
 65                  70                  75                  80 cag gcg ctg gag ccg ctg ccc atc gtg tac tac gtg ggc cgc aag ccc   288
Gln Ala Leu Glu Pro Leu Pro Ile Val Tyr Tyr Val Gly Arg Lys Pro
                 85                  90                  95 aag gtg gag cag ctg tcc aac atg atc gtg cgc tcc tgc aag tgc agc   336
Lys Val Glu Gln Leu Ser Asn Met Ile Val Arg Ser Cys Lys Cys Ser
             100                 105                 110 t                                                                 337
```

<210> SEQ ID NO 30
<211> LENGTH: 112
<212> TYPE: PRT
<213> ORGANISM: Human

<400> SEQUENCE: 30

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
             20                  25                  30

Ile His Glu Pro Lys Gly Tyr His Ala Asn Phe Cys Leu Gly Pro Cys
         35                  40                  45

Pro Tyr Ile Trp Ser Leu Asp Thr Gln Tyr Ser Lys Val Leu Ala Leu
     50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
             100                 105                 110
```

<210> SEQ ID NO 31
<211> LENGTH: 339
<212> TYPE: DNA
<213> ORGANISM: Human
<220> FEATURE:
<221> NAME/KEY: CDS
<222> LOCATION: (1)...(336)

<400> SEQUENCE: 31

```
gct ttg gat gcg gcc tat tgc ttt aga aat gtg cag gat aat tgc tgc    48
Ala Leu Asp Ala Ala Tyr Cys Phe Arg Asn Val Gln Asp Asn Cys Cys
 1               5                  10                  15 cta cgt cca ctt tac att gat ttc aag agg gat cta ggg tgg aaa tgg    96
Leu Arg Pro Leu Tyr Ile Asp Phe Lys Arg Asp Leu Gly Trp Lys Trp
```

```
              20                  25                  30
ata cac gaa ccc aaa ggg tac aat gcc aac ttc tgt gct gga gca tgc      144
Ile His Glu Pro Lys Gly Tyr Asn Ala Asn Phe Cys Ala Gly Ala Cys
         35                  40                  45 ccg tat tta tgg agt tca gac act cag cac agc agg gtc ctg agc tta      192
Pro Tyr Leu Trp Ser Ser Asp Thr Gln His Ser Arg Val Leu Ser Leu
     50                  55                  60 tat aat acc ata aat cca gaa gca tct gct tct cct tgc tgc gtg tcc      240
Tyr Asn Thr Ile Asn Pro Glu Ala Ser Ala Ser Pro Cys Cys Val Ser
 65                  70                  75                  80 caa gat tta gaa cct cta acc att ctc tac tac att ggc aaa aca ccc      288
Gln Asp Leu Glu Pro Leu Thr Ile Leu Tyr Tyr Ile Gly Lys Thr Pro
                 85                  90                  95 caa gat tta gaa cct cta acc att ctc tac tac att ggc aaa aca ccc      336
Gln Asp Leu Glu Pro Leu Thr Ile Leu Tyr Tyr Ile Gly Lys Thr Pro
            100                 105                 110 taa                                                                  339
```

<210> SEQ ID NO 32
<211> LENGTH: 112
<212> TYPE: PRT
<213> ORGANISM: Human

<400> SEQUENCE: 32

```
Ala Leu Asp Ala Ala Tyr Cys Phe Arg Asn Val Gln Asp Asn Cys Cys
 1               5                  10                  15

Leu Arg Pro Leu Tyr Ile Asp Phe Lys Arg Asp Leu Gly Trp Lys Trp
                 20                  25                  30

Ile His Glu Pro Lys Gly Tyr Asn Ala Asn Phe Cys Ala Gly Ala Cys
         35                  40                  45

Pro Tyr Leu Trp Ser Ser Asp Thr Gln His Ser Arg Val Leu Ser Leu
     50                  55                  60

Tyr Asn Thr Ile Asn Pro Glu Ala Ser Ala Ser Pro Cys Cys Val Ser
 65                  70                  75                  80

Gln Asp Leu Glu Pro Leu Thr Ile Leu Tyr Tyr Ile Gly Lys Thr Pro
                 85                  90                  95

Gln Asp Leu Glu Pro Leu Thr Ile Leu Tyr Tyr Ile Gly Lys Thr Pro
            100                 105                 110
```

<210> SEQ ID NO 33
<211> LENGTH: 339
<212> TYPE: DNA
<213> ORGANISM: Human
<220> FEATURE:
<221> NAME/KEY: CDS
<222> LOCATION: (1)...(336)

<400> SEQUENCE: 33

```
gct ttg gac acc aat tac tgc ttc cgc aac ttg gag gag aac tgc tgt       48
Ala Leu Asp Thr Asn Tyr Cys Phe Arg Asn Leu Glu Glu Asn Cys Cys
 1               5                  10                  15 gtg cgc ccc ctc tac att gac ttc cga cag gat ctg ggc tgg aag tgg       96
Val Arg Pro Leu Tyr Ile Asp Phe Arg Gln Asp Leu Gly Trp Lys Trp
                 20                  25                  30 gtc cat gaa cct aag ggc tac tat gcc aac ttc tgc tca ggc cct tgc      144
Val His Glu Pro Lys Gly Tyr Tyr Ala Asn Phe Cys Ser Gly Pro Cys
         35                  40                  45 cca tac ctc cgc agt gca gac aca acc cac agc acg gtg ctg gga ctg      192
Pro Tyr Leu Arg Ser Ala Asp Thr Thr His Ser Thr Val Leu Gly Leu
     50                  55                  60
```

```
tac aac act ctg aac cct gaa gca tct gcc tcg cct tgc tgc gtg ccc      240
Tyr Asn Thr Leu Asn Pro Glu Ala Ser Ala Ser Pro Cys Cys Val Pro
 65                  70                  75                  80 cag gac ctg gag ccc ctg acc atc ctg tac tat gtt ggg agg acc ccc      288
Gln Asp Leu Glu Pro Leu Thr Ile Leu Tyr Tyr Val Gly Arg Thr Pro
                 85                  90                  95 aaa gtg gag cag ctc tcc aac atg gtg gtg aag tct tgt aaa tgt agc      336
Lys Val Glu Gln Leu Ser Asn Met Val Val Lys Ser Cys Lys Cys Ser
            100                 105                 110 tga                                                                   339
```

<210> SEQ ID NO 34
<211> LENGTH: 112
<212> TYPE: PRT
<213> ORGANISM: Human

<400> SEQUENCE: 34

```
Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
            100                 105                 110
```

<210> SEQ ID NO 35
<211> LENGTH: 406
<212> TYPE: DNA
<213> ORGANISM: Human
<220> FEATURE:
<221> NAME/KEY: CDS
<222> LOCATION: (1)...(342)

<400> SEQUENCE: 35

```
caa gcc aaa cac aaa cag cgg aaa cgc ctt aag tcc agc tgt aag aga       48
Gln Ala Lys His Lys Gln Arg Lys Arg Leu Lys Ser Ser Cys Lys Arg
 1               5                  10                  15 cac cct ttg tac gtg gac ttc agt gac gtg ggg tgg aat gac tgg att       96
His Pro Leu Tyr Val Asp Phe Ser Asp Val Gly Trp Asn Asp Trp Ile
                20                  25                  30 gtg gct ccc ccg ggg tat cac gcc ttt tac tgc cac gga gaa tgc cct      144
Val Ala Pro Pro Gly Tyr His Ala Phe Tyr Cys His Gly Glu Cys Pro
            35                  40                  45 ttt cct ctg gct gat cat ctg aac tcc act aat cat gcc att gtt cag      192
Phe Pro Leu Ala Asp His Leu Asn Ser Thr Asn His Ala Ile Val Gln
        50                  55                  60 acg ttg gtc aac tct gtt aac tct aag att cct aag gca tgc tgt gtc      240
Thr Leu Val Asn Ser Val Asn Ser Lys Ile Pro Lys Ala Cys Cys Val
 65                  70                  75                  80 ccg aca gaa ctc agt gct atc tcg atg ctg tac ctt gac gag aat gaa      288
Pro Thr Glu Leu Ser Ala Ile Ser Met Leu Tyr Leu Asp Glu Asn Glu
                 85                  90                  95
```

```
aag gtt gta tta aag aac tat cag gac atg gtt gtg gag ggt tgt ggg      336
Lys Val Val Leu Lys Asn Tyr Gln Asp Met Val Val Glu Gly Cys Gly
            100                 105                 110 tgt cgc tagtacagca aaattaaata cataaatata tatatatata tatattttag        392
Cys Arg aaaaaagaaa aaaa                                                       406
```

<210> SEQ ID NO 36
<211> LENGTH: 114
<212> TYPE: PRT
<213> ORGANISM: Human

<400> SEQUENCE: 36

```
Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Asn His Ala Ile Val Gln
     50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 37
<211> LENGTH: 589
<212> TYPE: DNA
<213> ORGANISM: Human
<220> FEATURE:
<221> NAME/KEY: CDS
<222> LOCATION: (1)...(549)

<400> SEQUENCE: 37

```
tct act ggg gtc ttg ctg cct ctg cag aac aac gag ctt cct ggg gca      48
Ser Thr Gly Val Leu Leu Pro Leu Gln Asn Asn Glu Leu Pro Gly Ala
 1               5                  10                  15 gaa tac cag tat aaa aag gat gag gtg tgg gag gag aga aag cct tac      96
Glu Tyr Gln Tyr Lys Lys Asp Glu Val Trp Glu Glu Arg Lys Pro Tyr
                20                  25                  30 aag acc ctt cag gct cag gcc cct gaa aag agt aag aat aaa aag aaa      144
Lys Thr Leu Gln Ala Gln Ala Pro Glu Lys Ser Lys Asn Lys Lys Lys
            35                  40                  45 cag aga aag ggg cct cat cgg aag agc cag acg ctc caa ttt gat gag      192
Gln Arg Lys Gly Pro His Arg Lys Ser Gln Thr Leu Gln Phe Asp Glu
     50                  55                  60 cag acc ctg aaa aag gca agg aga aag cag tgg att gaa cct cgg aat      240
Gln Thr Leu Lys Lys Ala Arg Arg Lys Gln Trp Ile Glu Pro Arg Asn
65                  70                  75                  80 tgc gcc agg aga tac ctc aag gta gac ttt gca gat att ggc tgg agt      288
Cys Ala Arg Arg Tyr Leu Lys Val Asp Phe Ala Asp Ile Gly Trp Ser
                85                  90                  95 gaa tgg att atc tcc ccc aag tcc ttt gat gcc tat tat tgc tct gga      336
Glu Trp Ile Ile Ser Pro Lys Ser Phe Asp Ala Tyr Tyr Cys Ser Gly
            100                 105                 110
```

```
gca tgc cag ttc ccc atg cca aag tct ttg aag cca tca aat cat gct   384
Ala Cys Gln Phe Pro Met Pro Lys Ser Leu Lys Pro Ser Asn His Ala
    115                 120                 125 acc atc cag agt ata gtg aga gct gtg ggg gtc gtt cct ggg att cct   432
Thr Ile Gln Ser Ile Val Arg Ala Val Gly Val Val Pro Gly Ile Pro
130                 135                 140 gag cct tgc tgt gta cca gaa aag atg tcc tca ctc agt att tta ttc   480
Glu Pro Cys Cys Val Pro Glu Lys Met Ser Ser Leu Ser Ile Leu Phe
145                 150                 155                 160 ttt gat gaa aat aag aat gta gtg ctt aaa gta tac cct aac atg aca   528
Phe Asp Glu Asn Lys Asn Val Val Leu Lys Val Tyr Pro Asn Met Thr
                165                 170                 175 gta gag tct tgc gct tgc aga taacctggca agaactcat ttgaatgctt       579
Val Glu Ser Cys Ala Cys Arg
            180 aattcaatct                                                        589

<210> SEQ ID NO 38
<211> LENGTH: 183
<212> TYPE: PRT
<213> ORGANISM: Human

<400> SEQUENCE: 38

Ser Thr Gly Val Leu Leu Pro Leu Gln Asn Asn Glu Leu Pro Gly Ala
1               5                   10                  15

Glu Tyr Gln Tyr Lys Lys Asp Glu Val Trp Glu Glu Arg Lys Pro Tyr
                20                  25                  30

Lys Thr Leu Gln Ala Gln Ala Pro Glu Lys Ser Lys Asn Lys Lys Lys
            35                  40                  45

Gln Arg Lys Gly Pro His Arg Lys Ser Gln Thr Leu Gln Phe Asp Glu
        50                  55                  60

Gln Thr Leu Lys Lys Ala Arg Arg Lys Gln Trp Ile Glu Pro Arg Asn
65                  70                  75                  80

Cys Ala Arg Arg Tyr Leu Lys Val Asp Phe Ala Asp Ile Gly Trp Ser
                85                  90                  95

Glu Trp Ile Ile Ser Pro Lys Ser Phe Asp Ala Tyr Tyr Cys Ser Gly
            100                 105                 110

Ala Cys Gln Phe Pro Met Pro Lys Ser Leu Lys Pro Ser Asn His Ala
        115                 120                 125

Thr Ile Gln Ser Ile Val Arg Ala Val Gly Val Val Pro Gly Ile Pro
    130                 135                 140

Glu Pro Cys Cys Val Pro Glu Lys Met Ser Ser Leu Ser Ile Leu Phe
145                 150                 155                 160

Phe Asp Glu Asn Lys Asn Val Val Leu Lys Val Tyr Pro Asn Met Thr
                165                 170                 175

Val Glu Ser Cys Ala Cys Arg
            180

<210> SEQ ID NO 39
<211> LENGTH: 348
<212> TYPE: DNA
<213> ORGANISM: Human

<400> SEQUENCE: 39
agccctaagc atcactcaca gcgggccagg aagaagaata agaactgccg gcgccactcg     60
ctctatgtgg acttcagcga tgtgggctgg aatgactgga ttgtgccccc accaggctac   120
caggccttct actgccatgg ggactgcccc tttccactgg ctgaccacct caactcaacc   180
```

```
aaccatgcca ttgtgcagac cctggtcaat tctgtcaatt ccagtatccc caaagcctgt    240
tgtgtgccca ctgaactgag tgccatctcc atgctgtacc tggatgagta tgataaggtg    300
gtactgaaaa attatcagga gatggtagta gagggatgtg ggtgccgc                 348
```

<210> SEQ ID NO 40
<211> LENGTH: 116
<212> TYPE: PRT
<213> ORGANISM: Human

<400> SEQUENCE: 40

```
Ser Pro Lys His His Ser Gln Arg Ala Arg Lys Lys Asn Lys Asn Cys
  1               5                  10                  15

Arg Arg His Ser Leu Tyr Val Asp Phe Ser Asp Val Gly Trp Asn Asp
             20                  25                  30

Trp Ile Val Ala Pro Pro Gly Tyr Gln Ala Phe Tyr Cys His Gly Asp
         35                  40                  45

Cys Pro Phe Pro Leu Ala Asp His Leu Asn Ser Thr Asn His Ala Ile
     50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                 85                  90                  95

Tyr Asp Lys Val Val Leu Lys Asn Tyr Gln Glu Met Val Val Glu Gly
            100                 105                 110

Cys Gly Cys Arg
        115
```

<210> SEQ ID NO 41
<211> LENGTH: 507
<212> TYPE: DNA
<213> ORGANISM: Human
<220> FEATURE:
<221> NAME/KEY: CDS
<222> LOCATION: (1)...(414)

<400> SEQUENCE: 41

```
gca gcc aac aaa cga aaa aat caa aac cgc aat aaa tcc agc tct cat      48
Ala Ala Asn Lys Arg Lys Asn Gln Asn Arg Asn Lys Ser Ser Ser His
  1               5                  10                  15 cag gac tcc tcc aga atg tcc agt gtt gga gat tat aac aca agt gag      96
Gln Asp Ser Ser Arg Met Ser Ser Val Gly Asp Tyr Asn Thr Ser Glu
             20                  25                  30 caa aaa caa gcc tgt aag aag cac gaa ctc tat gtg agc ttc cgg gat     144
Gln Lys Gln Ala Cys Lys Lys His Glu Leu Tyr Val Ser Phe Arg Asp
         35                  40                  45 ctg gga tgg cag gac tgg att ata gca cca gaa gga tac gct gca ttt     192
Leu Gly Trp Gln Asp Trp Ile Ile Ala Pro Glu Gly Tyr Ala Ala Phe
     50                  55                  60 tat tgt gat gga gaa tgt tct ttt cca ctt aac gcc cat atg aat gcc     240
Tyr Cys Asp Gly Glu Cys Ser Phe Pro Leu Asn Ala His Met Asn Ala
 65                  70                  75                  80 acc aac cac gct ata gtt cag act ctg gtt cat ctg atg ttt cct gac     288
Thr Asn His Ala Ile Val Gln Thr Leu Val His Leu Met Phe Pro Asp
                 85                  90                  95 cac gta cca aag cct tgt tgt gct cca acc aaa tta aat gcc atc tct     336
His Val Pro Lys Pro Cys Cys Ala Pro Thr Lys Leu Asn Ala Ile Ser
            100                 105                 110 gtt ctg tac ttt gat gac agc tcc aat gtc att ttg aaa aaa tat aga     384
```

```
Val Leu Tyr Phe Asp Asp Ser Ser Asn Val Ile Leu Lys Lys Tyr Arg
            115                 120                 125 aat atg gta gta cgc tca tgt ggc tgc cac taatattaaa taatattgat        434
Asn Met Val Val Arg Ser Cys Gly Cys His
    130                 135 aataacaaaa agatctgtat taaggtttat ggctgcaata aaaagcatac tttcagacaa    494
acagaaaaaa aaa                                                      507

<210> SEQ ID NO 42
<211> LENGTH: 138
<212> TYPE: PRT
<213> ORGANISM: Human

<400> SEQUENCE: 42

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
            20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
    50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
        115                 120                 125

Asn Met Val Val Arg Ser Cys Gly Cys His
    130                 135

<210> SEQ ID NO 43
<211> LENGTH: 497
<212> TYPE: DNA
<213> ORGANISM: Human
<220> FEATURE:
<221> NAME/KEY: CDS
<222> LOCATION: (1)...(417)

<400> SEQUENCE: 43 tca gcc tcc agc cgg cgc cga caa cag agt cgt aat cgc tct acc cag    48
Ser Ala Ser Ser Arg Arg Arg Gln Gln Ser Arg Asn Arg Ser Thr Gln
1               5                   10                  15 tcc cag gac gtg gcg cgg gtc tcc agt gct tca gat tac aac agc agt    96
Ser Gln Asp Val Ala Arg Val Ser Ser Ala Ser Asp Tyr Asn Ser Ser
            20                  25                  30 gaa ttg aaa aca gcc tgc agg aag cat gag ctg tat gtg agt ttc caa    144
Glu Leu Lys Thr Ala Cys Arg Lys His Glu Leu Tyr Val Ser Phe Gln
        35                  40                  45 gac ctg gga tgg cag gac tgg atc att gca ccc aag ggc tat gct gcc    192
Asp Leu Gly Trp Gln Asp Trp Ile Ile Ala Pro Lys Gly Tyr Ala Ala
    50                  55                  60 aat tac tgt gat gga gaa tgc tcc ttc cca ctc aac gca cac atg aat    240
Asn Tyr Cys Asp Gly Glu Cys Ser Phe Pro Leu Asn Ala His Met Asn
65                  70                  75                  80 gca acc aac cac gcg att gtg cag acc ttg gtt cac ctt atg aac ccc    288
Ala Thr Asn His Ala Ile Val Gln Thr Leu Val His Leu Met Asn Pro
```

```
                    85                  90                  95
gag tat gtc ccc aaa ccg tgc tgt gcg cca act aag cta aat gcc atc        336
Glu Tyr Val Pro Lys Pro Cys Cys Ala Pro Thr Lys Leu Asn Ala Ile
            100                 105                 110 tcg gtt ctt tac ttt gat gac aac tcc aat gtc att ctg aaa aaa tac        384
Ser Val Leu Tyr Phe Asp Asp Asn Ser Asn Val Ile Leu Lys Lys Tyr
        115                 120                 125 agg aat atg gtt gta aga gct tgt gga tgc cac taactcgaaa ccagatgctg      437
Arg Asn Met Val Val Arg Ala Cys Gly Cys His
    130                 135 gggacacaca ttctgccttg gattcctaga ttacatctgc cttaaaaaaa cacggaagca      497

<210> SEQ ID NO 44
<211> LENGTH: 139
<212> TYPE: PRT
<213> ORGANISM: Human

<400> SEQUENCE: 44

Ser Ala Ser Ser Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
                20                  25                  30

Glu Leu Lys Thr Ala Cys Arg Lys His Glu Leu Tyr Val Ser Phe Gln
            35                  40                  45

Asp Leu Gly Trp Gln Asp Trp Ile Ile Ala Pro Lys Gly Tyr Ala Ala
        50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 45
<211> LENGTH: 476
<212> TYPE: DNA
<213> ORGANISM: Human
<220> FEATURE:
<221> NAME/KEY: CDS
<222> LOCATION: (1)...(417)

<400> SEQUENCE: 45 tcc acg ggg agc aaa cag cgc agc cag aac cgc tcc aag acg ccc aag        48
Ser Thr Gly Ser Lys Gln Arg Ser Gln Asn Arg Ser Lys Thr Pro Lys
1               5                   10                  15 aac cag gaa gcc ctg cgg atg gcc aac gtg gca gag aac agc agc agc        96
Asn Gln Glu Ala Leu Arg Met Ala Asn Val Ala Glu Asn Ser Ser Ser
                20                  25                  30 gac cag agg cag gcc tgt aag aag cac gag ctg tat gtc agc ttc cga       144
Asp Gln Arg Gln Ala Cys Lys Lys His Glu Leu Tyr Val Ser Phe Arg
        35                  40                  45 gac ctg ggc tgg cag gac tgg atc atc gcg cct gaa ggc tac gcc gcc       192
Asp Leu Gly Trp Gln Asp Trp Ile Ile Ala Pro Glu Gly Tyr Ala Ala
    50                  55                  60 tac tac tgt gag ggg gag tgt gcc ttc cct ctg aac tcc tac atg aac       240
```

```
Tyr Tyr Cys Glu Gly Glu Cys Ala Phe Pro Leu Asn Ser Tyr Met Asn
65                  70                  75                  80 gcc acc aac cac gcc atc gtg cag acg ctg gtc cac ttc atc aac ccg      288
Ala Thr Asn His Ala Ile Val Gln Thr Leu Val His Phe Ile Asn Pro
                85                  90                  95 gaa acg gtg ccc aag ccc tgc tgt gcg ccc acg cag ctc aat gcc atc      336
Glu Thr Val Pro Lys Pro Cys Cys Ala Pro Thr Gln Leu Asn Ala Ile
            100                 105                 110 tcc gtc ctc tac ttc gat gac agc tcc aac gtc atc ctg aag aaa tac      384
Ser Val Leu Tyr Phe Asp Asp Ser Ser Asn Val Ile Leu Lys Lys Tyr
        115                 120                 125 aga aac atg gtg gtc cgg gcc tgt ggc tgc cac tagctcctcc gagaattcag    437
Arg Asn Met Val Val Arg Ala Cys Gly Cys His
    130                 135 acccttggg gccaagtttt tctggatcct ccattgctc                            476
```

```
<210> SEQ ID NO 46
<211> LENGTH: 139
<212> TYPE: PRT
<213> ORGANISM: Human

<400> SEQUENCE: 46

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

```
<210> SEQ ID NO 47
<211> LENGTH: 103
<212> TYPE: PRT
<213> ORGANISM: Human
<220> FEATURE:
<221> NAME/KEY: VARIANT
<222> LOCATION: (1)...(103)
<223> OTHER INFORMATION: Xaa = Any Amino Acid

<400> SEQUENCE: 47

Cys Xaa Xaa Xaa Xaa Leu Xaa Val Xaa Phe Xaa Asp Xaa Gly Trp Xaa
1               5                   10                  15

Xaa Trp Ile Xaa Xaa Pro Xaa Xaa Xaa Xaa Xaa Tyr Cys Xaa Gly
            20                  25                  30

Xaa Cys Xaa Phe Pro Xaa Xaa Xaa Xaa Xaa Xaa Xaa Asn His Ala
        35                  40                  45

Xaa Xaa Gln Xaa Xaa Val Xaa Xaa Xaa Xaa Xaa Xaa Xaa Xaa Pro
    50                  55                  60
```

Xaa Xaa Cys Cys Xaa Pro Xaa Xaa Xaa Xaa Xaa Ser Xaa Leu Xaa
65                  70                  75                  80

Xaa Asp Xaa Xaa Xaa Xaa Val Xaa Leu Lys Xaa Tyr Xaa Xaa Met Xaa
                85                  90                  95

Val Xaa Xaa Cys Xaa Cys Xaa
            100

<210> SEQ ID NO 48
<211> LENGTH: 103
<212> TYPE: PRT
<213> ORGANISM: Human
<220> FEATURE:
<221> NAME/KEY: VARIANT
<222> LOCATION: (1)...(103)
<223> OTHER INFORMATION: Xaa = Any Amino Acid

<400> SEQUENCE: 48

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Cys Xaa Xaa
                20                  25                  30

Xaa Cys Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Cys Cys Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Cys Xaa Cys Xaa
            100

<210> SEQ ID NO 49
<211> LENGTH: 4
<212> TYPE: PRT
<213> ORGANISM: Human
<220> FEATURE:
<221> NAME/KEY: VARIANT
<222> LOCATION: (1)...(4)
<223> OTHER INFORMATION: Xaa = Any Amino Acid

<400> SEQUENCE: 49

Arg Xaa Xaa Arg
1

<210> SEQ ID NO 50
<211> LENGTH: 9
<212> TYPE: PRT
<213> ORGANISM: Human

<400> SEQUENCE: 50

Trp Arg Glu Pro Ser Phe Cys Ala Leu
1               5

<210> SEQ ID NO 51
<211> LENGTH: 9
<212> TYPE: PRT
<213> ORGANISM: Human

```
<400> SEQUENCE: 51

Trp Arg Glu Pro Ser Phe Met Ala Leu
1               5
```